US012065695B2

(12) United States Patent
Mandell

(10) Patent No.: US 12,065,695 B2
(45) Date of Patent: *Aug. 20, 2024

(54) POLYNUCLEOTIDE AMPLIFICATION USING CRISPR-CAS SYSTEMS

(71) Applicant: Illumina, Inc., San Diego, CA (US)

(72) Inventor: Jeffrey G. Mandell, La Jolla, CA (US)

(73) Assignee: Illumina, Inc., San Diego, CA (US)

(*) Notice: Subject to any disclaimer, the term of this patent is extended or adjusted under 35 U.S.C. 154(b) by 1208 days.

This patent is subject to a terminal disclaimer.

(21) Appl. No.: 16/735,372

(22) Filed: Jan. 6, 2020

(65) Prior Publication Data

US 2020/0199664 A1 Jun. 25, 2020

Related U.S. Application Data

(63) Continuation of application No. 15/524,962, filed as application No. PCT/US2015/059959 on Nov. 10, 2015, now Pat. No. 10,577,649.

(60) Provisional application No. 62/078,355, filed on Nov. 11, 2014.

(51) Int. Cl.
*C12Q 1/6853* (2018.01)
*C12N 15/10* (2006.01)
*C12N 15/63* (2006.01)
*C12N 15/90* (2006.01)

(52) U.S. Cl.
CPC .......... *C12Q 1/6853* (2013.01); *C12N 15/10* (2013.01); *C12N 15/63* (2013.01); *C12N 15/90* (2013.01); *C12Q 2521/101* (2013.01); *C12Q 2521/301* (2013.01); *C12Q 2522/101* (2013.01); *C12Q 2525/155* (2013.01)

(58) Field of Classification Search
CPC ........................... C12Q 1/6853; C12Q 1/6844
See application file for complete search history.

(56) References Cited

U.S. PATENT DOCUMENTS

| | | |
|---|---|---|
| 4,683,195 A | 7/1987 | Mullins |
| 4,883,750 A | 11/1989 | Whiteley |
| 5,034,506 A | 7/1991 | Summerton |
| 5,432,272 A | 7/1995 | Benner |
| 5,476,930 A | 12/1995 | Letsinger |
| 5,523,204 A | 6/1996 | Singer |
| 5,536,649 A | 7/1996 | Fraiser |
| 5,591,609 A | 1/1997 | Auerbach |
| 5,593,826 A | 1/1997 | Fung |
| 5,614,389 A | 3/1997 | Auerbach |
| 5,624,825 A | 4/1997 | Walker |
| 5,631,147 A | 5/1997 | Lohman |
| 5,648,211 A | 7/1997 | Fraiser |
| 5,733,752 A | 3/1998 | Lohman |
| 5,744,311 A | 4/1998 | Fraiser |
| 5,756,702 A | 5/1998 | Lohman |
| 5,773,733 A | 6/1998 | Tuan |
| 5,786,183 A | 7/1998 | Ryder |
| 5,834,202 A | 8/1998 | Auerbach |
| 5,849,547 A | 12/1998 | Cleuziat |
| 5,871,921 A | 2/1999 | Landegren |
| 5,874,260 A | 2/1999 | Cleuziat |
| 5,916,779 A | 6/1999 | Pearson |
| 6,063,604 A | 5/2000 | Wick |
| 6,087,133 A | 7/2000 | Dattagupta |
| 6,124,120 A | 9/2000 | Lizardi |
| 6,210,891 B1 | 4/2001 | Nyren |
| 6,214,587 B1 | 4/2001 | Dattagupta |
| 6,218,151 B1 | 4/2001 | Cleuziat |
| 6,238,868 B1 | 5/2001 | Carrino |
| 6,251,639 B1 | 6/2001 | Kum |
| 6,258,568 B1 | 7/2001 | Nyren |
| 6,261,808 B1 | 7/2001 | Auerbach |
| 6,274,320 B1 | 8/2001 | Rothberg |
| 6,280,949 B1 | 8/2001 | Lizardi |
| 6,309,833 B1 | 10/2001 | Edman |
| 6,326,173 B1 | 12/2001 | Edman |
| 6,410,278 B1 | 6/2002 | Notomi |
| 6,448,017 B1 | 9/2002 | Auerbach |
| 7,001,792 B2 | 2/2006 | Sauer |
| 7,057,026 B2 | 6/2006 | Barnes |
| 7,115,400 B1 | 10/2006 | Adessi |
| 7,211,414 B2 | 5/2007 | Hardin |
| 7,244,559 B2 | 7/2007 | Rothberg |
| 7,315,019 B2 | 1/2008 | Turner |
| 7,329,492 B2 | 2/2008 | Hardin |

(Continued)

FOREIGN PATENT DOCUMENTS

| | | |
|---|---|---|
| AU | 2000029442 | 12/2000 |
| CN | 103233028 | 8/2013 |

(Continued)

OTHER PUBLICATIONS

Ansorge, W.J. Next-generation DNA sequencing techniques. New Biotechnology 2009; 25: 195-203 (Year: 2009).*
Jeong et al. Isothermal DNA amplification in vitro: the helicase-dependent amplification system. Cellular and Molecular Life Sciences 2009; 66: 3325-3336. (Year: 2009).*
Kersting et al. Multiplex isothermal solid-phase recombinase polymerase amplification for the specific and fast DNA-based detection of three bacterial pathogens. Microchimica Acta 2014; 181: 1715-1723 (Year: 2014).*
Agarwal, *Protocols for Polynucleotides and Analogs*, Humana Press, 1994, Table of Contents Only.

(Continued)

*Primary Examiner* — Angela M. Bertagna
(74) *Attorney, Agent, or Firm* — Knobbe Martens Olson & Bear LLP

(57) ABSTRACT

A method for amplifying a target nucleic acid including providing a system having a crRNA or a derivative thereof, and a Cas protein or a variant thereof. The crRNA or the derivative thereof contains a target-specific nucleotide region substantially complementary to a region of the target nucleic acid, and contacting the target nucleic acid with the system to form a complex.

17 Claims, 3 Drawing Sheets

Specification includes a Sequence Listing.

(56) References Cited

U.S. PATENT DOCUMENTS

| | | | |
|---|---|---|---|
| 7,405,281 | B2 | 7/2008 | Xu |
| 7,413,857 | B2 | 8/2008 | Dahl |
| 7,595,883 | B1 | 9/2009 | El Gamal |
| 7,754,429 | B2 * | 7/2010 | Rigatti .................. C12Q 1/6874 435/6.1 |
| 7,985,565 | B2 | 7/2011 | Mayer |
| 10,577,649 | B2 * | 3/2020 | Mandell ................. C12N 15/10 |
| 2005/0153333 | A1 | 7/2005 | Sooknanan |
| 2005/0191698 | A1 | 9/2005 | Chee |
| 2008/0108082 | A1 | 5/2008 | Rank |
| 2009/0026082 | A1 | 1/2009 | Rothberg |
| 2009/0127589 | A1 | 5/2009 | Rothberg |
| 2010/0120098 | A1 | 5/2010 | Grunenwald |
| 2010/0137143 | A1 | 6/2010 | Rothberg |
| 2010/0282617 | A1 | 11/2010 | Rothberg |
| 2014/0356867 | A1 * | 12/2014 | Peter ........................ C12N 9/22 536/23.1 |
| 2016/0017396 | A1 * | 1/2016 | Cann ...................... C12Q 1/683 506/26 |

FOREIGN PATENT DOCUMENTS

| | | |
|---|---|---|
| CN | 104017821 | 9/2014 |
| EP | 1218542 | 7/2002 |
| WO | WO 1991/06678 | 5/1991 |
| WO | WO 1995/23875 | 9/1995 |
| WO | WO 2000/28082 | 5/2000 |
| WO | WO 2000/56877 | 9/2000 |
| WO | WO 2002/16639 | 2/2002 |
| WO | WO 2004/018497 | 3/2004 |
| WO | WO 2007/123744 | 11/2007 |
| WO | WO 2010/048605 | 4/2010 |
| WO | WO 2012/058096 | 5/2015 |

OTHER PUBLICATIONS

Barrangou et al., CRISPR Provides Acquired Resistance Against Viruses in Prokaryotes, 2007, *Science* 315:1709-12.

Beloglazova et al., Structure and activity of the Cas3 HD nuclease MJ0384, an effector enzyme of the CRISPR interference, 2011, *EMBO J* 30:616-627.

Bentley et al., Accurate whole human genome sequencing using reversible terminator chemistry, *Nature* 456:53-59 (2008).

Boeke and Corces, Transcription and Reverse Transcription of Retrotransposons, 1989, *Annu Rev Microbiol.* 43: 403-34.

Bolotin et al., Clustered regularly interspaced short palindrome repeats (CRISPRs) have spacers of extra chromosomal origin, 2005, *Microbiology* 151 :2551-61.

Brouns et al., Small CRISPR RNAs guide antiviral defense in prokaryotes, 2008, *Science* 321: 960-4.

Brown et al., Retroviral integration: Structure of the initial covalent product and its precursor, and a role for the viral IN protein, 1989, *Proc Nat/Acad Sci USA* 86: 2525-9.

Cockroft et al., A single-molecule nanopore device detects DNA polymerase activity with single-nucleotide resolution, 2008, *J. Am. Chem. Soc.*, 130, 818-820.

Colegio et al., In vitro transposition system for efficient generation of random mutants of campylobacter jejuni, 2001, *J. Bacteriol.* 183: 2384-8.

Craig, Transposon Tn7, Review in: *Curr Top Microbiol Immunol.* 1996, 204: 27-48.

Craig, V(D)J Recombination and Transposition: Closer than Expected, 1996, *Science* 271 : 1512.

Craw and Balachandran, Isothermal nucleic acid amplification technologies for point-of-care diagnostics: a critical review, *Lab Chip*, 2012, 12: 2469-2486.

Deamer et al., Nanopores and nucleic acids: prospects for ultrarapid sequencing, 2000, *Trends Biotechnol.*, 18, 147-151.

Deamer et al., Characterization of Nucleic Acids by Nanopore Analysis, 2002, *Acc. Chem. Res.* 35:817-825.

Devine and Boeke, Efficient integration of artificial transposons into plasmid targets in vitro: a useful tool for DNA mapping, sequencing and genetic analysis, 1994, *Nucleic Acids Res.*, 22: 3765-72.

Englisch, Angew. 'Chemically Modified Oligonucleotides as Probes and Inhibitors' *Chem. Int. Ed. Engl.* 30:613-29, 1991.

Fujita Toshitsugu et al. "Efficient isolation of specific genomic regions and identification of associated proteins by engineered DNA-binding molecule-mediated chromatin immunoprecipitation (enChIP) using CRISPR", Biochemical and Biophysical Research Communications, 439: I, 2013, 132-136.

Gao, Feng et al., DNA-guided genome editing using the Natronobacterium gregoryi Argonaute, *Nature Biotechnology*, doi: 10.1038/nbt.3547 (May 2, 2016).

Gill and Ghaemi, 'Nucleic Acid Isothermal Amplification Technologies—A Review', *Nucleosides, Nucleotides, and Nucleic Acids*, 2008, 27: 224-243.

Gloor, Gene Targeting in *Drosophila*, 2004, *Methods Mol. Biol.* 260: 97-114.

Gootenberg, Jonathan et al. 'Nucleic acid detection with CRISPR-Cas13a/C2c2' *Science*. 0.1126/science.aam9321 (2017).

Goryshin and Reznikoff, Tn5 in vitro transposition, 1998, *J. Biol. Chem.*, 273: 7367.

Haft et al., A guild of 45 CRISPR—associated (Cas) protein families and multiple CRISPR/Cas subtypes exist in prokaryotic genomes, *PLoS Comput Biol.*, 2005, 1(6): e60.

Hale et al., RNA-guided RNA cleavage by a CRISPR RNA-Cas protein complex, 2009, *Cell* 139:945-956.

Hatoum-Aslan et al. "Mature clustered, regularly interspaced, short palindromic repeats RNA (crRNA) length is measured by a ruler mechanism anchored at the precursor processing site", *Proceedings of The National Academy of Sciences*, 108:52, 2011, 21218-21222.

Healy, Nanopore-based single-molecule DNA analysis, 2007, Nanomed. 2, 459-481.

Howard et al., Helicase dissociation and annealing of RNA-DNA hybrids by *Escherichia coli* Cas3 protein, Biochem J., 2011, 439(1):85-95.

Ichikawa and Ohtsubo, In vitro transposition of transposon Tn3, 1990, *J Biol. Chem.* 265: 18829-32.

Jinek et al., A programmable Dual-RNA-Guided DNA Endonuclease in Adaptive Bacterial Immunity, 2012, *Science* 337, 816-821.

Jore et al., 'Structural basis for CRISPR RNA-guided DNA recognition by Cascade' Nature Structural & Molecular Biology, 2011, 18,529-536.

Kirby et al., Cryptic plasmids of mycobacterium avium: Tn552 to the rescue, 2002, *Mol. Microbiol.* 43: 173-86.

Kleckner et al., Tn10 and IS10 Transposition and Chromosome Rearrangements: Mechanism and Regulation In Vivo and In Vitro 1996, *Curr Top Microbiol Immunol.* 204: 49-82.

Korlach et al., Selective aluminum passivation for targeted immobilization of single DNA polymerase molecules in zero-mode waveguide nanostructures, 2008, *Proc. Natl. Acad. Sci. USA* 105, 1176-1181.

Koshkin et al., 'LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition', *Tetrahedron* 54:3607-30, 1998.

Lakowicz, "Principles of Fluorescence Spectroscopy," Plenum Publishing Corporation, 2nd edition (Jul. 1, 1999), Table of Contents Only.

Lampe et al., A purified mariner transposase is sufficient to mediate transposition in vitro, 1996, *EMBO J.* 15: 5470-9.

Levene et al., Zero-mode waveguides for single-molecule analysis at high concentrations, 2003, *Science* 299, 682-686.

Li et al., DNA molecules and configurations in a solid-state nanopore microscope, 2003, Nat. Mater. 2:611-615.

Lundquist et al., Parallel confocal detection of single molecules in real time, 2008, *Opt. Lett.* 33, 1026-1028.

Makarova et al., Evolution and classification of the CRISPR-Cas systems, 2011, *Nat Rev Microbiol* 9:467-77.

Marraffini and Sontheimer, CRISPR interference limits horizontal gene transfer in *Staphylococci* by targeting DNA, 2008, *Science* 322:1843-1845.

(56) References Cited

OTHER PUBLICATIONS

Marraffini and Sontheimer, CRISPR interference: RNA-directed adaptive immunity in bacteria and archaea, 2010, *Nat Rev Genet.* 11(3): 181-190.

Mizuuchi, In Vitro Transposition of Bacteriophage Mu: A Biochemical Approach to a Novel Replication Reaction, 1983, *Cell*, 35: 785.

Mojica et al., 'Intervening Sequences of Regularly Spaced Prokaryotic Repeats Derive from Foreign Genetic Elements' 2005, *J Mol Evol* 60:174-82.

Mullis et al., Specific enzymatic amplification of DNA in vitro: the polymerase chain reaction, Cold Spring Harbor Symp. Quant. Biol., 51: 263 (1986).

Ohtsubo & Sekine, Bacterial Insertion Sequences, Curr. Top. Microbiol. Immunol. 204: 1-26 (1996).

Plasterk, The Tc1/mariner Transposon Family, 1996, *Curr Top Microbiol Immunol* 204: 125-43.

Ronaghi et al., DNA Sequencing: A sequencing method based on real-time pyrophosphate, 1998, *Science* 281(5375) 363-365.

Ronaghi, Pyrosequencing sheds light on DNA sequencing, 2001, *Genome Res.* 11(1), 3-11.

Ronaghi, et al., Real-time DNA sequencing using detection of pyrophosphate release, 1996, *Analytical Biochemistry* 242(1), 84-9.

Savilahti et al., The phase Mu transpososome core: DNA requirements for assembly and function, 1995, *EMBO J.*, 14: 4893.

Sinkunas et al., Cas3 is a single-stranded DNA nuclease and ATP-dependent helicase in the CRISPR/Cas immune system, 2011, *EMBO J* 30:1335-1342.

Soni et al., Progress toward Ultrafast DNA sequencing Using Solid-State Nanpores, 2007, *Clin. Chem.*, 53, 1996-200.

"Locked Nucleic Acid (LNA™) Phosphoramidites" The Glen Report, 16(2):5, p. 5 (2003).

Tyagi et al., Molecular beacons: probes that fluoresce upon hybridization, Nature Biotechnology, 1996, 303-308.

Verma and F. Eckstein, Modified oligonucleotides: Synthesis and strategy for users, *Ann. Rev. Biochem.* 1998, 67:99-134.

Wetmur and Davidson, Kinetics of renaturation of DNA, Mol. Biol. 31:349 (1968).

Zhang et al., Expanding the catalog of cas genes with metagenomes, *Nucl. Acids Res.*, 2014, 10.1093/nar/gkt1262.

Written Opinion issued Feb. 2, 2016 for PCT/US2015/059959.

International Search Report issued Feb. 2, 2016 for PCT/US2015/059959.

Li, et al., Advances in isothermal amplification: novel strategies inspired by biological processes, Biosensors and Bioelectronics, 64:196-211 (2015).

Feng, et al., Function and organization of CRISPR-Cas Systems and application in biotechnology, Journal of Sichuan Normal University (Natural Science) 37(2): 268-281 (2014).

\* cited by examiner

Standard P5 & P7:
P5 seq: 5' AATGATACGGCGACCACCGAGATCTACAC '3 (SEQ ID No. 1)
P7 seq: 5' CAAGCAGAAGACGGCATACGAGAT '3 (SEQ ID No. 2)

PAM-Modified P5 & P7:
P5 seq: 5' CCN AATGATACGGCGACCACCGAGATCTACAC '3 (SEQ ID No. 3)
P7 seq: 5' CCN CAAGCAGAAGACGGCATACGAGAT '3 (SEQ ID No. 4)

Truncated, PAM-Modified P5 & P7:
P5 seq: 5' CCN AATGATACGGCGACCACCGAGATCTACAC '3 (SEQ ID No. 5)
P7 seq: 5' CCN CAAGCAGAAGACGGCATACGAGAT '3 (SEQ ID No. 6)

Guide RNAs:
P5 targeting: 5' UCGGUGGUCGCCGUAUCAUU 3' (SEQ ID No. 7)
P7 targeting: 5' CGUAUGCCGUCUUCUGCUUG 3' (SEQ ID No. 8)

Figure 1A

POLYNUCLEOTIDE AMPLIFICATION USING CRISPR-CAS SYSTEMS

RELATED APPLICATIONS

This application is a continuation of U.S. application Ser. No. 15/524,962 filed May 5, 2017, now U.S. Pat. No. 10,577,649 issued Mar. 3, 2020 which is the U.S. national phase of PCT/US2015/059959 filed Nov. 10, 2015 and published in English as WO 2016/077350 on May 19, 2016 which claims priority to U.S. Prov. App. No. 62/078,355 filed on Nov. 11, 2014 which are each hereby incorporated by reference in its entirety.

REFERENCE TO SEQUENCE LISTING

The present application is being filed along with a Sequence Listing in electronic format. The Sequence Listing is provided as a filed entitled ILLINC388C1SEQLISTING, created Mar. 8, 2024, which is approximately 3734 bytes in size. The information in the electronic format of the Sequence Listing is incorporated herein by reference in its entirety.

FIELD

The present disclosure relates generally to methods for amplifying polynucleotides, and more specifically to methods for amplifying polynucleotides using CRISPR-Cas systems and applications thereof.

BACKGROUND

Nucleic acid amplification is a key step of many nucleic acid based processes such as nucleic acid sequencing. Most currently used nucleic acid amplification methods, e.g., those used in cluster generation in the next generation sequencing, require both temperature cycling and fluid exchanges. Isothermal amplification, on the other hand, can be time and energy efficient by eliminating temperature ramp and equilibration times. Several isothermal amplification methods have been developed, e.g., recombinase polymerase amplification (RPA) based isothermal amplification. These isothermal amplification systems usually lack the desired speed and efficiency ideally suitable for some applications. Furthermore, some systems require additional enzymes and reagents including ATP. Thus, there remains a need in the art for convenient, rapid, and efficient isothermal nucleic acid amplification methods. The present disclosure addresses this need by providing methods for amplifying nucleic acid using CRISPR-Cas systems. Related advantages are provided as well.

Clustered regularly interspaced short palindromic repeats (CRISPRs) are involved in an interference pathway that protects cells from bacteriophages and conjugative plasmids in many bacteria and archaea (Marraffini and Sontheimer, 2010, *Nat Rev Genet.* 11(3): 181-190). CRISPR consists of arrays of short repeat sequences interspaced by unique variable DNA sequences of similar size called spacers, which often originate from phage or plasmid DNA (Barrangou et al., 2007, *Science* 315:1709-12; Bolotin et al., 2005, *Microbiology* 151:2551-61; Mojica et al., 2005, *J Mol Evol* 60:174-82). Thus, CRISPR sequences provide an adaptive, heritable record of past infections and may be transcribed into CRISPR RNAs (crRNAs)—small RNAs that target invasive nucleic acids (Marraffini and Sontheimer, 2010, *Nat Rev Genet.* 11(3): 181-190). CRISPRs are often associated with CRISPR-associated (Cas) genes that code for proteins related to CRISPRs. Cas proteins can provide mechanisms for destroying invading foreign nucleic acids targeted by crRNAs. CRISPRs together with Cas (CRISPR-associated) genes comprise an adaptive immune system that provides acquired resistance against invading foreign nucleic acids in bacteria and archaea (Barrangou et al., 2007, *Science* 315:1709-12).

SUMMARY

The present disclosure provides methods for amplifying polynucleotides, and more specifically to methods for amplifying a target DNA sequence using CRISPR-Cas systems and applications thereof.

In one aspect, provided herein is a method for amplifying a target double-stranded nucleic acid including: (a) providing a system having: a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; (b) contacting the target double-stranded nucleic acid with the system to form a complex; (c) hybridizing a primer to a second strand of the target double-stranded nucleic acid, the primer containing a sequence complementary to a region of the second strand of the target double-stranded nucleic acid, and (d) extending a nucleic acid complementary to the second strand of the target double-stranded nucleic acid from the primer using a polymerase.

In some embodiments, the method provided herein further including repeating step (c) to step (d) for one or more times, e.g., until a desired degree of amplification is reached. In some embodiments, the method provided herein further including repeating step (a) to step (d) until a desired degree of amplification is reached.

In some embodiments, the target nucleic acid provided herein is a double-stranded DNA (dsDNA). In some embodiments, the target nucleic acid is a double-stranded RNA (dsRNA).

In some embodiments, the system is a Type I CRISPR-Cas system or a derivative thereof. In some embodiments, the system is a Type II CRISPR-Cas system or a derivative thereof. In some embodiments, the system is a Type III CRISPR-Cas system or a derivative thereof.

In some embodiments, the system further comprises a trans-activating crRNA (tracrRNA) or a derivative thereof. In some embodiments, the crRNA or the derivative thereof is a polynucleotide comprising a crRNA polynucleotide fused to a tracrRNA polynucleotide.

In some embodiments, the first strand of the target double-stranded nucleic acid contains a sequence complementary to a 5'-NGG protospacer-adjacent motif (PAM).

In some embodiments, the first strand of the target double-stranded nucleic acid contains a universal sequence, and wherein the crRNA or the derivative thereof contains a sequence complementary to a region of the universal sequence. In some embodiments, the primer contains a sequence of a region of the universal sequence.

In some embodiments, the universal sequence has a sequence of SEQ ID No. 3. In some embodiments, the crRNA contains a sequence of SEQ ID No.7. In some embodiments, the universal sequence has a sequence of SEQ ID No. 5.

In some embodiments, the universal sequence has a sequence of SEQ ID No. 4. In some embodiments, the crRNA contains a sequence of SEQ ID No.8. In some embodiments, the universal sequence has a sequence of SEQ ID No. 6.

In some embodiments, the Cas protein or the variant thereof is a Cas9 protein or a variant thereof. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, the first mutation is D10A and the second mutation is H840A. In some embodiments, the Cas protein or the variant thereof is a Cascade protein or a variant thereof. In some embodiments, the Cas protein or the variant thereof is a Cas3 protein or a variant thereof.

In some embodiments, the polymerase is a strand-displacing polymerase. In some embodiments, the polymerase is selected from a group consisting of Bst, Bsu, and Phi29.

In some embodiments, the method provided herein further comprises: applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments, and incorporating a universal primer sequence into each of the plurality of target nucleic acid fragments, wherein the crRNA or the derivative thereof contains a target-specific nucleotide region complementary to a region of the universal primer.

In some embodiments, the universal primer is incorporated into the plurality of target nucleic acid fragments by a PCR reaction. In some embodiments, the universal primer has sequence complementary to a 5'-NGG protospacer-adjacent motif (PAM).

In some embodiments, the universal sequence has a sequence of SEQ ID No. 3. In some embodiments, the crRNA contains a sequence of SEQ ID No.7. In some embodiments, the universal sequence has a sequence of SEQ ID No.5.

In some embodiments, the universal primer has a sequence of SEQ ID No. 4. In some embodiments, the crRNA contains a sequence of SEQ ID No.8. In some embodiments, the universal sequence has a sequence of SEQ ID No. 6.

In some embodiments, two universal primers are incorporated into two ends of each of the plurality of target nucleic acid fragments. In some embodiments, the two universal primers have sequences of SEQ ID No.3 and SEQ ID No.4. In some embodiments, the two universal primers have sequences of SEQ ID No.5 and SEQ ID No.6.

In some embodiments, the target double-stranded nucleic acid is linearly amplified. In some embodiments, the target double-stranded nucleic acid is exponentially amplified.

In some embodiments, provided herein is a method for amplifying a target double-stranded nucleic acid comprising: (a) providing a first system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a target-specific nucleotide region complementary to a region of a first strand of the target double-stranded nucleic acid; (b) providing second system having: a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, the method provided herein further includes repeating step (a) and step (e) for one or more times, e.g., until a desired degree of amplification is reached.

In some embodiments, the target nucleic acid is a double-stranded DNA (dsDNA). In some embodiments, the target nucleic acid is a double-stranded RNA (dsRNA).

In some embodiments, the first system or the second system is a Type I CRISPR-Cas system or a derivative thereof. In some embodiments, the first system or the second system is a Type II CRISPR-Cas system or a derivative thereof. In some embodiments, the first system or a second system is a Type III CRISPR-Cas system or a derivative thereof.

In some embodiments, the first system or the second system further comprises a trans-activating crRNA (tracrRNA) or a derivative thereof. In some embodiments, the crRNA or the derivative thereof of the first system or the second system is a polynucleotide comprising a crRNA polynucleotide fused to a tracrRNA polynucleotide. In some embodiments, the first strand and the second strand of the target double-stranded nucleic acid contain a sequence complementary to a 5'-NGG protospacer-adjacent motif (PAM).

In some embodiments, the first strand of the target double-stranded nucleic acid contains a first universal sequence, and wherein the crRNA or the derivative thereof of the first system contains a sequence complementary to a region of the first universal sequence, and the second strand of the target double-stranded nucleic acid contains a second universal sequence, and wherein the crRNA or the derivative thereof of the second system contains a sequence complementary to a region of the second universal sequence.

In some embodiments, the first primer contains a sequence of a region of the first universal sequence, and the second primer contains a sequence of a region of the second universal sequence. In some embodiments, the first universal sequence (which contains a first primer) has a sequence of SEQ ID No. 3, the crRNA or the derivative thereof of the first system contains a sequence of SEQ ID No.7, and the first primer contains a sequence of SEQ ID No. 5, and the second universal sequence (which contains a second primer) has a sequence of SEQ ID No. 4, the crRNA or derivative thereof of the second system contains a sequence of SEQ ID No.8, and the second primer contains a sequence of SEQ ID No. 6.

In some embodiments, the Cas protein or the variant thereof of the first system or the second system is a Cas9 protein or a variant thereof. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, the first mutation is D10A and the second mutation is H840A. In some embodiments, the Cas protein or the variant thereof of the first system or the second system is a Cascade protein or a variant thereof. In some embodiments, the Cas protein or the variant thereof of the first system or the second system is a Cas3 protein or a variant thereof.

In some embodiments, the polymerase is a strand-displacing polymerase. In some embodiments, the polymerase is selected from a group consisting of Bst, Bsu, and Phi29.

In some embodiments, the target nucleic acid is genomic DNA. In some embodiments, the target nucleic acid contains chromosomal DNA or a fragment thereof. In some embodiments, the target nucleic acid comprises a genome or a partial genome.

In some embodiments, the method provided herein further includes sequencing the target nucleic acid or target nucleic acid fragments. In some embodiments, the sequencing comprises use of one or more of sequencing by synthesis, bridge PCR, chain termination sequencing, sequencing by hybridization, nanopore sequencing, and sequencing by ligation.

BRIEF DESCRIPTION OF THE DRAWINGS

FIG. 1A shows the primers designed according to the present methods for amplifying DNA fragments containing the entirety or portions of Illumina universal sequencing primer adaptors P5 and P7. The primers can be added using the Nextera (Illumina, Inc.) library preparation method.

DETAILED DESCRIPTION

Figure 1B:
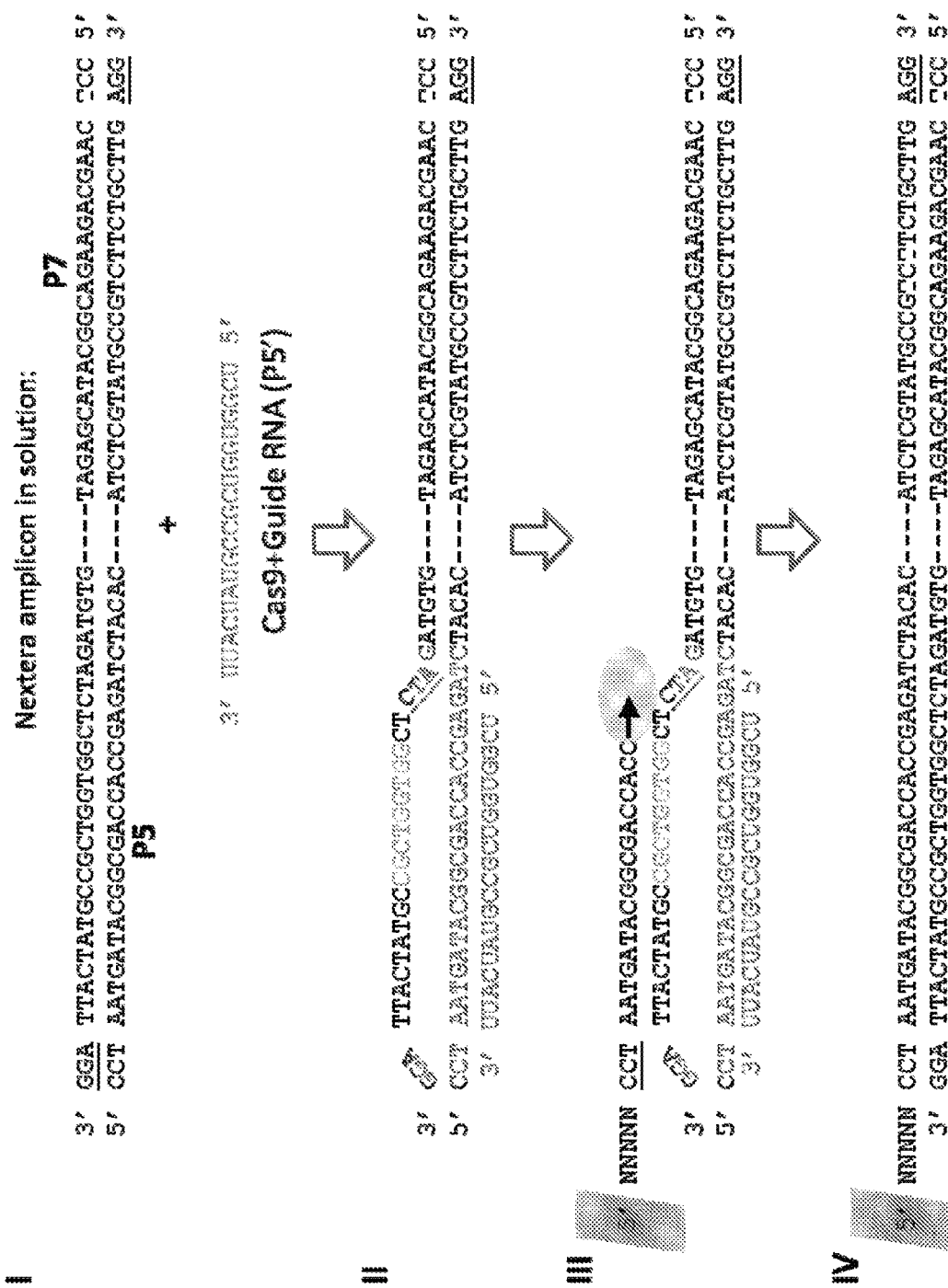
FIG. 1B illustrates one round of Cas9-mediated linear amplification using a crRNA targeting a modified P5 primer. Panel (I) depicts the DNA to be amplified which possesses appropriate primer sequences P5 (SEQ ID NO:09) and P7 (SEQ ID NO:10). The guide RNA targeting P5, bound to Cas9, is also shown as P5' (SEQ ID NO:07). Panel (II) shows the R loop created by Cas9 after the guide RNA has hybridized to the first strand. Panel (III) illustrates the immobilized P5 primer (SEQ ID NO:12) hybridizing to the displaced second strand, followed by polymerase extension. Panel (IV) shows the resulting extended primer P5 (SEQ ID NO:13) at 5' end of the amplicon, and a P7 sequence (SEQ ID NO:04) at 3' end of the amplicon. The resulting amplicon can be re-targeted by Cas9+crRNA as shown in the step depicted in panel (II).

The present disclosure provides methods for rapid and efficient amplification of target nucleic acid using CRISPR-Cas systems.

Nucleic acid amplification is a step of many nucleic acid based processes such as next generation sequencing. Currently the polymerase chain reaction (PCR) is the most widely used method for DNA amplification for, e.g., detection and identification of infectious diseases, genetic disorders and other research purposes. A PCR reaction typically uses two oligonucleotide primers, which are hybridized to the 3' ends of a duplex target nucleic acid sequence, and a DNA polymerase, which can extend the annealed primers by adding on deoxyribonucleoside triphosphates (dNTPs) to generate double-stranded nucleic acid products. Gill and Ghaemi, *Nucleosides, Nucleotides, and Nucleic Acids*, 2008, 27: 224-243. However, a PCR reaction requires thermocycling to separate the two DNA strands. Similarly, many currently used nucleic acid amplification methods, e.g., those used in cluster generation in the next generation sequencing, require both temperature cycling and fluid exchanges.

Several isothermal amplification methods have been developed in order to eliminate temperature ramp and equilibration times, such as recombinase polymerase amplification (RPA) based isothermal amplification, transcription mediated amplification, nucleic acid sequence-based amplification, signal mediated amplification of RNA, strand displacement amplification, rolling circle amplification, loop-mediated amplification of DNA, isothermal multiple displacement amplification, helicase-dependent amplification, single primer isothermal amplification, and circular helicase-dependent amplification, as described in Gill and Ghaemi, *Nucleosides, Nucleotides, and Nucleic Acids*, 2008, 27: 224-243.

For example, in a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is very similar to Self-Sustained Sequence Replication (3SR) and Nucleic Acid Sequence Based Amplification (NASBA), but varies in the enzymes employed. Id. For another example, helicase-dependent amplification (HDA) utilizes a thermostable helicase (Tte-UvrD) rather than heat to unwind dsDNA to create single-strands that are then available for hybridization and extension of primers by polymerase. Reaction times have been shown to be over 1 hour to amplify products 70-120 base pairs in length. Id. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. Id. For yet another example, a strand displacement amplification (SDA) combines the ability of a restriction endonuclease to nick the unmodified strand of its target DNA and an exonulease-deficient DNA polymerase to extend the 3' end at the nick and displace the downstream DNA strand. Id. Other exemplary isothermal amplification methods include, but not limited to, those described in Craw and Balachandran, *Lab Chip,* 2012, 12: 2469-2486.

However, these currently developed isothermal amplification systems usually lack the desired speed and efficiency ideally suitable for some applications. Furthermore, some systems require additional enzymes and reagents including ATP. Thus, there remains a need in the art for convenient, rapid, and efficient isothermal nucleic acid amplification methods. The present disclosure addresses this need by providing methods for amplifying nucleic acid using CRISPR-Cas systems. For example, one advantage provided by the present methods is that Cas protein recognizes target nucleic acid without consuming ATP or energy investment, and thus the methods herein provide for cost and time efficient isothermal amplification methods.

Definitions

As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the singular forms "a", "an" and "the" include plural referents unless the content clearly dictates otherwise. Thus, for example, reference to "a protein" includes a mixture of two or more proteins, and the like.

As used herein, the term "about" or "approximately" means within 5% of a given value or range.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g, $H^+$, $NH_4^+$, trialkylammonium, tetraalkylammonium, $Mg^{2+}$, $Na^+$ and the like. A nucleic acid can be a polynucleotide or a oligonucleotide. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotides analogs. Nucleic acid typically ranges in size from a few monomeric units, e.g, 5-40, to several thousands of monomeric nucleotide units. Nucleic acids include, but are not limited to, genomic DNA, cDNA, hnRNA, mRNA, IRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "target nucleic acid" is intended to mean a nucleic acid that is the object of an analysis or action. The analysis or action includes subjecting the nucleic acid to copying, amplification, sequencing and/or other procedure for nucleic acid interrogation. A target nucleic acid can include nucleotide sequences additional to the target sequence to be analyzed. For example, a target nucleic acid can include one or more adapters, including an adapter that functions as a primer binding site, that flank(s) a target nucleic acid sequence that is to be analyzed. A target nucleic acid hybridized to a capture oligonucleotide or capture primer can contain nucleotides that extend beyond the 5' or 3' end of the capture oligonucleotide in such a way that not all of the target nucleic acid is amenable to extension.

As used herein, the term "target specific" when used in reference to a guide RNA, a crRNA or a derivative thereof, or other nucleotide is intended to mean a polynucleotide that includes a nucleotide sequence specific to a target polynucleotide sequence, namely a sequence of nucleotides capable of selectively annealing to an identifying region of a target polynucleotide, e.g., a target DNA. Target specific nucleotide can have a single species of oligonucleotide, or it can include two or more species with different sequences. Thus, the target specific nucleotide can be two or more sequences, including 3, 4, 5, 6, 7, 8, 9 or 10 or more different sequences. In one embodiment, a crRNA or the derivative thereof contains a target-specific nucleotide region complementary to a region of the target DNA sequence. In one embodiment, a crRNA or the derivative thereof may contain other nucleotide sequences besides a target-specific nucleotide region. In one embodiment, the other nucleotide sequences may be from a tracrRNA sequence.

As used herein, the term "complementary" when used in reference to a polynucleotide is intended to mean a polynucleotide that includes a nucleotide sequence capable of selectively annealing to an identifying region of a target polynucleotide under certain conditions. As used herein, the term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions can also contribute to duplex stability. Conditions under which a polynucleotide anneals to complementary or substantially complementary regions of target nucleic acids are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968). Annealing conditions will depend upon the particular application, and can be routinely determined by persons skilled in the art, without undue experimentation.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions will typically include salt concentrations of less than about 1 M, more usually less than about 500 mM and may be less than about 200 mM. A hybridization buffer includes a buffered salt solution such as 5% SSPE, or other such buffers known in the art. Hybridization temperatures can be as low as 5° C., but are typically greater than 22° C, and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances, and may be determined routinely by those skilled in the art.

In the context of "polynucleotides," the terms "variant" and "derivative" as used herein refer to a polynucleotide that comprises a nucleotide sequence of a polynucleotide or a fragment of a polynucleotide, which has been altered by the introduction of nucleotide substitutions, deletions or additions. A variant or a derivative of a polynucleotide can be a fusion polynucleotide which contains part of the nucleotide sequence of a polynucleotide. The term "variant" or "derivative" as used herein also refers to a polynucleotide or a fragment thereof, which has been chemically modified, e.g., by the covalent attachment of any type of molecule to the polynucleotide. For example, but not by way of limitation, a polynucleotide or a fragment thereof can be chemically modified, e.g., by acetylation, phosphorylation, methylation, etc. The variants or derivatives are modified in a manner that is different from naturally occurring or starting nucleotide or polynucleotide, either in the type or location of the molecules attached. Variants or derivatives further include deletion of one or more chemical groups which are naturally present on the nucleotide or polynucleotide. A variant or a derivative of a polynucleotide or a fragment of a polynucleotide can be chemically modified by chemical modifications using techniques known to those of skill in the art, including, but not limited to specific chemical cleavage, acetylation, formulation, etc. Further, a variant or a derivative of a polynucleotide or a fragment of a polynucleotide can contain one or more dNTPs or nucleotide analogs. A polynucleotide variant or derivative may possess a similar or identical function as a polynucleotide or a fragment of a polynucleotide described herein. A polynucleotide variant or derivative may possess an additional or different function compared with a polynucleotide or a fragment of a polynucleotide described herein.

As used herein, the term "dNTP" refers to deoxynucleoside triphosphates. NTP refers to ribonucleotide triphosphates such as those used to synthesize crRNA or tracrRNA. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

As used herein, the term "nucleotide analogs" refers to synthetic analogs having modified nucleotide base portions, modified pentose portions, and/or modified phosphate portions, and, in the case of polynucleotides, modified internucleotide linkages, as generally described elsewhere (e.g., Scheit, *Nucleotide Analogs*, John Wiley, New York, 1980; Englisch, *Angew. Chem. Int. Ed. Engl.* 30:613-29, 1991; Agarwal, *Protocols for Polynucleotides and Analogs*, Humana Press, 1994; and S. Verma and F. Eckstein, *Ann. Rev. Biochem.* 67:99-134, 1998). Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., The Glen Report, 16(2):5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., *Organic Chem.*, 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles.

The terms "polymerase chain reaction," or "PCR," as used herein, refers to a procedure wherein small amounts of a nucleic acid, e.g., RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, N Y, 1989).

As used herein, the terms "ligation," "ligating," and grammatical equivalents thereof are intended to mean to form a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921, incorporated herein by reference in their entireties. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "adapter" is a single-stranded or a double-stranded nucleic acid molecule that can be linked to the end of other nucleic acids. In one embodiment, an adapter is a short, chemically synthesized, double-stranded nucleic acid molecule which can be used to link the ends of two other nucleic acid molecules. In one embodiment, an adaptor is a double-stranded nucleic acid (e.g., oligonucleotides) that comprises single-stranded nucleotide overhangs at the 5' and/or 3' ends. In some embodiments, the single-stranded overhangs are 1, 2 or more nucleotides. In some embodiments, adaptors comprise additional nucleic acid sequence for cloning or analysis of "inserts." In some embodiments, adaptors comprise labels or affinity tags for analysis or purification of "inserts." The term "insert" refers to a nucleic acid sequence of interest. In some embodiments, inserts are double-stranded DNAs that comprise single stranded nucleotide overhangs at the 5' and/or 3' ends. In some embodiments, the single stranded overhangs are 1, 2 or more nucleotides.

As used herein, the term "CRISPR-Cas system" refers to an enzyme system including a guide RNA sequence that contains a nucleotide sequence complementary or substantially complementary to a region of a target polynucleotide, and a protein with nuclease activity. CRISPR-Cas systems include Type I CRISPR-Cas system, Type II CRISPR-Cas system, Type III CRISPR-Cas system, and derivatives thereof. CRISPR-Cas systems include engineered and/or programmed nuclease systems derived from naturally accruing CRISPR-Cas systems. CRISPR-Cas systems may contain engineered and/or mutated Cas proteins. CRISPR-Cas systems may contain engineered and/or programmed guide RNA.

As used herein, the term "guide RNA" refers to a RNA containing a sequence that is complementary or substantially complementary to a region of a target DNA sequence. A guide RNA may contain nucleotide sequences other than the region complementary or substantially complementary to a region of a target DNA sequence. A guide RNA may be a crRNA or a derivative thereof, e.g., a crRNA: tracrRNA chimera.

As used herein, the term "nuclease" refers to an enzyme capable of cleaving the phosphodiester bonds between the nucleotide subunits of nucleic acids; the term "endonuclease" refers to an enzyme capable of cleaving the phosphodiester bond within a polynucleotide chain; and the term "nickase" refers to an endonuclease which cleaves only a single strand of a DNA duplex. The term "Cas9 nickase" refers to a nickase derived from a Cas9 protein, typically by inactivating one nuclease domain of Cas9 protein.

In the context of a polypeptide, the terms "variant" and "derivative" as used herein refer to a polypeptide that comprises an amino acid sequence of a polypeptide or a fragment of a polypeptide, which has been altered by the introduction of amino acid residue substitutions, deletions or additions. A variant or a derivative of a polypeptide can be a fusion protein which contains part of the amino acid sequence of a polypeptide. The term "variant" or "derivative" as used herein also refers to a polypeptide or a fragment of a polypeptide, which has been chemically modified, e.g., by the covalent attachment of any type of molecule to the polypeptide. For example, but not by way of limitation, a polypeptide or a fragment of a polypeptide can be chemically modified, e.g., by glycosylation, acetylation, pegylation, phosphorylation, amidation, derivatization by known protecting/blocking groups, proteolytic cleavage, linkage to a cellular ligand or other protein, etc. The variants or derivatives are modified in a manner that is different from naturally occurring or starting peptide or polypeptides, either in the type or location of the molecules attached. Variants or derivatives further include deletion of one or more chemical groups which are naturally present on the peptide or polypeptide. A variant or a derivative of a polypeptide or a fragment of a polypeptide can be chemically modified by chemical modifications using techniques known to those of skill in the art, including, but not limited to specific chemical cleavage, acetylation, formulation, metabolic synthesis of tunicamycin, etc. Further, a variant or a derivative of a polypeptide or a fragment of a polypeptide can contain one or more non-classical amino acids. A polypeptide variant or derivative may possess a similar or identical function as a polypeptide or a fragment of a polypeptide described herein. A polypeptide variant or derivative may possess an additional or different function compared with a polypeptide or a fragment of a polypeptide described herein.

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, the term "primer" refers to an oligonucleotide primer, whether natural or synthetic, which is capable of acting as a point of initiation of nucleic acid synthesis when placed under conditions in which primer extension (not limited in number of extended bases) is initiated. A primer can be a single-stranded oligodeoxyribonucleotide. The length of a primer can range from about 10 to about 50 nucleotides, for example 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides. A primer need not reflect the exact sequence of the template but must be sufficiently complementary to hybridize with a template for primer elongation to occur. A primer can be labeled, if desired, by incorporating a label that is detectable by, for example, spectroscopic, photochemical, biochemical, immunochemical, or chemical means. Exemplary labels include, but are not limited to biotin, amine, radiolabels (e.g., 32P), fluorescent dyes, electron-dense reagents, enzymes (as commonly used in ELISAS), or biotin.

As used herein, the term "linear amplification" refers to an amplification process that uses multiple cycles of primer extension reactions to amplify a target nucleic acid. With linear amplification, the abundance of a transcript increases proportionately with the number of cycles and scales linearly. An example of a linear amplification procedure is LCR, the aRNA method of Phillips and Eberwine, supra, and the linear amplification method described herein. Unlike exponential amplification, the amount of the amplification products does not grow exponentially. For example, in an ideal 4 hour linear amplification reaction whose copying rate is 2000 copies per minute, 2000 copies of template DNA will yield 960,000,000 copies.

As used herein, the term "exponential amplification" refers to an amplification procedure where the product (i.e., amplicon) doubles with every reaction cycle. "Exponential amplification" is a non-linear amplification that results in exponential growth in the number of nucleic acid copies present. For example, exponential amplification can occur when primer extension initiates from both ends of an amplicon in one amplification cycle. For example, PCR is an exponential amplification procedure. For example, in an ideal PCR reaction with 30 cycles, 2 copies of template DNA will yield $2^{30}$ or 1,073,741,824 copies.

As used herein, the term "polymerase" refers to a protein that is able to catalyze the specific incorporation of nucleotides to extend a 3' hydroxyl terminus of a primer molecule, such as, for example, the template oligonucleotide, against a nucleic acid target sequence. The polymerase can be, for example, thermophilic so that it is active at an elevated reaction temperature. It can also, for example, have strand displacement capabilities.

Methods for Amplifying Polynucleotides

In one aspect, the present disclosure provides a method for CRISPR-Cas system mediated amplification. The methods provided herein is partially based on that binding of a guide RNA to a region of a target double-stranded nucleic acid disrupts the interaction between the two strands of the target nucleic acid, and thereby creates a loop structure (also called "R-loop") exposing the strand non-complementary to the guide RNA. This exposed strand can be subjected to hybridization with primer for extension by an appropriate polymerase, e.g., in a nucleic acid amplification process. As illustrated in Example 1, this loop structure created by CRISPR-Cas systems, e.g., systems containing Cas9 or Cascade proteins, can be accessible to other enzymes. Thus, the loop structure can be further utilized as a template to initiate primer hybridization and interact with polymerase enzymes for amplification.

In some embodiments, the present disclosure provides a method for amplifying a target double-stranded nucleic acid including providing a system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; contacting the target double-stranded nucleic acid with the system to form a complex; hybridizing a primer to a second strand of the target double-stranded nucleic acid, the primer containing a sequence complementary to a region of the second strand of the target double-nucleic acid, and extending a nucleic acid complementary to the second strand of the target double-stranded nucleic acid from the primer using a polymerase.

The methods provided herein can be used in various amplification methods, including but not limited to, linear nucleic acid amplification and exponential nucleic acid amplification.

In some embodiments, the target nucleic acid is amplified linearly according to the methods provided herein. For example, in some embodiments, the method provided herein further includes repeating hybridizing a primer to the second strand of the target double-stranded nucleic acid, and extending a nucleic acid complementary to the second strand of the target double-stranded nucleic acid from the primer using a polymerase for one or more times, e.g., until a desired amount of amplification is achieved.

In other embodiments, the target nucleic acid is amplified exponentially. In exemplary exponential nucleic acid amplification, the product (i.e., amplicon) doubles with every reaction cycle. "Exponential amplification" is a non-linear amplification that results in exponential growth in the number of nucleic acid copies present. Typically, in an exponential amplification, primer extension (or copying) occurs from both ends of an amplicon. To ensure that the newly created strand has a primer binding sites at both ends, in an exponential amplification, the 3' end of the new synthesized nucleic acid contains the reverse complement of a primer, and the ends of the template are usually copied in each amplification cycle.

The cycle number of the reactions according to the present methods depends on the applications and the desired amount of the amplification products. In some embodiments, cycle number is 5 to 100. In some embodiments, the cycle number is 10 to 90. In some embodiments, the cycle number is 20 to 80. In some embodiments, the cycle number is 30 to 70. In some embodiments, the cycle number is 40 to 60. Exemplary cycle number includes 10, 15, 20, 25, 30, 35, 40, 45, and 50. Cycles need not be synchronized between amplicons, as they are in a PCR reaction where the start of each cycle is controlled by changing the temperature. Cycles, as used herein, thus refers to the average number of rounds of amplification an amplicon undergoes.

In some embodiments, the initialization step includes provides multiple CRISPR-Cas systems to the target nucleic acid to open the double-stranded nucleic acid structure at two or more targeted sequences and to form two or more R-Loop structures. The initialization step does not require heating the reaction, as required in a PCR reaction, because this initialization step is enzyme driven. The next step according to the present methods involves providing and annealing primers targeted to the R-Loop regions to form relatively stable nucleic acid-nucleic acid interaction, e.g., DNA-DNA hybrids. Typically, stable nucleic acid-nucleic acid hybrids are formed when the primer sequence has substantial complementarity the template sequence. Then one or more polymerases bind to the primer-template hybrid and begins nucleic acid synthesis in an extension/elongation step. In some embodiments, the temperature at this extension/elongation step depends on the polymerase used. At this step the polymerase synthesizes a new nucleic acid strand complementary to the template strand by adding dNTPs that are complementary to the template. In some embodiments, when DNA polymerase is used, the reaction condenses the 5'-phosphate group of the dNTPs with the 3'-hydroxyl group at the end of the nascent (extending) DNA strand. The extension time depends both on the polymerase used and on the length of the nucleic acid fragment to be amplified. One or more of these steps can be repeated for one or more times, e.g., until a desired amount of amplification is achieved.

To permit exponential growth of the amplified products, it is beneficial that the newly created nucleic acid product in each cycle contains primer binding sites at both ends. In some embodiments, the 3' end of the newly synthesized molecule is the reverse complement of a primer. In some embodiments, two primers, each targeting to one end of a target nucleic acid, can be used in an exponential amplification. In some embodiments, it is also beneficial that the primer is designed in such way that it can be targeted by the CRISPR-Cas systems provided herein—that is the primer can be targeted by the guide RNA, e.g., crRNA, of the CRISPR-Cas systems so that the CRISPR-Cas systems can be repeatedly used to bind to the target nucleic acid to initiate a new round of amplification.

Thus, in some embodiments, two or more CRISPR-Cas systems are used to initiate primer binding at both ends of a target nucleic acid. In some embodiments, provided herein is a method for amplifying a target double-stranded nucleic acid including: (a) providing a first system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a target-specific nucleotide region complementary to a region of a first strand of the target double-stranded nucleic acid; (b) providing second system having: a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, primer hybridization and extension by polymerase steps are repeated for one or more times, e.g., until a desired degree of amplification is reached.

In other embodiments, the method provided herein is used for multiplex amplification. As used herein, the term "multiplex amplification" refers to the amplification of more than one nucleic acid of interest, e.g., an amplification of multiple sequences from the same sample. The term "multiplex amplification" also refers to the amplification of one or more sequences present in multiple samples either simultaneously or in step-wise fashion. Thus, in some embodiments, two or more target nucleic acid sequences are being amplified in an amplification reaction, and the amplification reaction comprises the appropriate templates and enzymes to amplify at least two target nucleic acid sequences. One application of the multiplex amplification provided herein is to detect two or more target sequences in a sample because multiplex amplification is cable of amplifying two or more target sequences. When only one of the target sequences is actually present in the sample being tested, the result of the multiplex amplification can be amplification of the only one sequence that is present. Multiplex amplification may utilize the same primer pairs to amplify a one or more intervening amplicon sequences. Alternatively, multiplex amplification may utilized one or more primer pairs.

In some embodiments, the double-stranded nucleic acid provided herein is a double-stranded DNA. In other embodiments, the double-stranded nucleic acid provided herein is a double-stranded RNA. In some embodiments, the target nucleic acid is genomic DNA. In other embodiments, the target nucleic acid contains chromosomal DNA or a fragment thereof. In yet other embodiments, the target nucleic acid comprises a genome or a partial genome.

In some embodiments, the systems provided herein are derived from CRISPR-Cas systems. CRISPR-Cas systems can generally be categorized into three major types (Type I-III), which are further subdivided into ten subtypes, based on core element content and sequences (Makarova et al., 2011, *Nat Rev Microbiol* 9:467-77). The two key elements of these CRISPR-Cas systems are Cas proteins and CRISPR RNA (crRNA). crRNA consists of short repeat sequences interspersed with spacer sequences derived from invader DNA. Cas proteins have various activities, e.g., nuclease activity. Thus, CRISPR-Cas systems provide mechanisms for targeting a specific sequence as well as certain enzyme activities upon the sequence.

A typical Type I CRISPR-Cas system contains Cas3 protein with separate helicase and DNase activities. For example, in the Type 1-E system, crRNAs are incorporated into a multisubunit effector complex called Cascade (CRISPR-associated complex for antiviral defense) (Brouns et al., 2008, *Science* 321: 960-4), which binds to the target DNA and triggers degradation by the Cas3 protein (Sinkunas et al., 2011, *EMBO J* 30:1335-1342; Beloglazova et al., 2011, *EMBO J* 30:616-627).

Type II CRISPR-Cas systems include the signature Cas9 protein, a single protein (about 160 KDa), capable of generating crRNA and cleaving the target DNA. The Cas9 protein typically contains two nuclease domains, a RuvC-like nuclease domain near the amino terminus and the HNH (or McrA-like) nuclease domain near the middle of the protein. Each nuclease domain of the Cas9 protein is specialized for cutting one strand of the double helix (Jinek et al., 2012, *Science* 337 (6096): 816-821).

Type III CRISPR-Cas systems contain polymerase and RAMP modules. Type III systems can be further divided into sub-types III-A and III-B. Type III-A CRISPR-Cas systems have been shown to target plasmids, and the polymerase-like proteins of Type III-A systems are involved in the cleavage of target DNA (Marraffini and Sontheimer, 2008, *Science* 322:1843-1845). Type III-B CRISPR-Cas systems have also been shown to target RNA (Hale et al., 2009, *Cell* 139:945-956).

Thus, in some embodiments, the system is a Type I CRISPR-Cas system or a derivative thereof. In other embodiments, the system is a Type II CRISPR-Cas system or a derivative thereof. In yet other embodiments, the system is a Type III CRISPR-Cas system or a derivative thereof.

The key elements of a CRISPR-Cas system include a guide RNA, e.g., a crRNA, and a Cas protein. The crRNA or the derivative thereof contains a target specific nucleotide region complementary or substantially complementary to a region of the target nucleic acid. In some embodiments, the crRNA or the derivative thereof contains a user-selectable RNA sequence that permits specific targeting of the enzyme to a complementary double-stranded DNA. In some embodiments, the user-selectable RNA sequence contains 20-50 nucleotides complementary or substantially complementary to a region of the target DNA sequence. In some embodiments, the user-selectable RNA sequence contains less than 20 nucleotides complementary or substantially complementary to a region of the target DNA sequence. Exemplary user-selectable RNA sequence contains 1, 2, 3, 4, 5, 6, 7, 8, 9, 10, 11, 12, 13, 14, 15, 16, 17, 18, or 19 nucleotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the crRNA and the region of the target nucleic acid. In some embodiments, there are three base pair mismatches between the target specific nucleotide region of the crRNA and the region of the target nucleic acid. In some embodiments, there are four base pair mismatches between the target specific nucleotide region of the crRNA and the region of the target nucleic acid. In some embodiments, there are five base pair mismatches between the target specific nucleotide region of the crRNA and the region of the target nucleic acid.

In some embodiments, the system provided herein further includes a trans-activating crRNA (tracrRNA) or a derivative thereof.

The CRISPR-Cas systems provided herein include engineered and/or programmed nuclease systems derived from naturally occurring CRISPR-Cas systems. CRISPR-Cas systems may include contain engineered and/or mutated Cas proteins. CRISPR-Cas systems may also contain engineered and/or programmed guide RNA. In some embodiments, the crRNA or the derivative thereof provided herein is a polynucleotide having a crRNA polynucleotide fused to a tracrRNA polynucleotide. A chimeric single-guided RNA (sgRNA) is described in Jinek et al., 2012, *Science* 337, 816-821, which is incorporated herein in its entirety. In one embodiment, the Cas protein or the variant thereof provided herein can be directed by a chimeric sgRNA to any genomic locus followed by a 5'-NGG protospacer-adjacent motif (PAM). For example, in some embodiments, crRNA and tracrRNA are synthesized by in vitro transcription, using a synthetic double stranded DNA template containing the T7 promoter. The tracrRNA has a fixed sequence, whereas the target sequence dictates part of crRNA's sequence. Equal molarities of crRNA and tracrRNA are mixed and heated at 55° C. for 30 seconds. Cas9 is added at the same molarity at 37° C. and incubated for 10 minutes with the RNA mix. 10-20 fold molar excess of Cas9 complex is then added to the target DNA. The binding reaction can occur within 15 minutes.

In some embodiments, the Cas protein or the variant thereof is a Cas9 protein or a variant thereof. Isolated Cas9-crRNA complex from the *S. thermophilus* CRISPR-Cas system as well as complex assembled in vitro from separate components demonstrate that it binds to both synthetic oligodeoxynucleotide and plasmid DNA bearing a nucleotide sequence complementary to the crRNA. It has been shown that Cas9 has two nuclease domains-RuvC- and HNH-active sites/nuclease domains, and these two nuclease domains are responsible for the cleavage of opposite DNA strands. In some embodiments, the Cas9 protein is derived from Cas9 protein of *S. thermophilus* CRISPR-Cas system. In some embodiments, the Cas9 protein is a multi-domain protein having about 1,409 amino acids residues.

In some embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In some embodiments, the Cas protein or the variant thereof is a Cascade protein or a variant thereof. Cascade complex in *E. coli* recognizes double-stranded DNA (dsDNA) targets in a sequence-specific manner. *E. coli* Cascade complex is a 405-kDa complex comprising five functionally essential CRISPR-associated (Cas) proteins (CasA1B2C6D1E1, also called Cascade protein) and a 61-nucleotide crRNA. The crRNA guides Cascade complex to dsDNA target sequences by forming base pairs with the complementary DNA strand while displacing the non-complementary strand to form an R-loop. Cascade recognizes target DNA without consuming ATP, which suggests that continuous invader DNA surveillance takes place without energy investment. Matthijs et al., Nature Structural & Molecular Biology, 2011, 18,529-536.

In some embodiments, the Cas protein or the variant thereof is a Cas3 protein or a variant thereof. *E. coli* Cas3 can catalyse ATP-independent annealing of RNA with DNA forming R-loops, and hybrid of RNA base-paired into duplex DNA. Cas3 protein can use gRNA that is longer than that for Cas9. Howard et al., Biochem J., 2011, 439(1):85- 95. Such longer RNA can permit easier access of other elements to the target DNA, e.g., access of a primer to be extended by polymerase. Another advantage provided by Cas3 protein is that Cas3 protein does not require a PAM sequence as Cas9, thus provides more flexibility for targeting desired sequence. R-loop formation by Cas3 may require magnesium as a co-factor. Howard et al., Biochem J., 2011, 439(1):85-95. Thus, in some embodiments, the system provided herein further comprises magnesium.

It should be appreciated that any CRISPR-Cas systems capable of disrupting the double stranded nucleic acid and creating a loop structure can be used in the present methods. For example, the Cas proteins provided herein may include, but not limited to, the Cas proteins described in Haft et al., *PLOS Comput Biol.*, 2005, 1(6): e60, and Zhang et al., *Nucl. Acids Res.*, 2013, 10.1093/nar/gkt1262. Some these CRISPR-Cas systems require that a specific sequence be present for these CRISPR-Cas systems to recognize and bind to the target sequence. For instance, Cas9 requires the presence of a 5'-NGG protospacer-adjacent motif (PAM). Thus, in some embodiments, a PAM sequence or a sequence complementary to a PAM sequence is engineered into the target nucleic acid for initiating the binding of the CRISPR-Cas systems to the target nucleic acid.

In some embodiments, the primer provided herein is a single-stranded oligodeoxyribonucleotide. In some embodiments, the length of a primer ranges from about 10 to about 50 nucleotides. Exemplary length of the primer provided herein is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, the primer provided herein has 100% base pair matching with a region of the target nucleic acid. In some embodiments, the primer provided herein has 90%-100%, 80%-100%, or 70%-100% base pair matching with the region of the target nucleic acid. In some embodiments, there is one base pair mismatch between the primer and the region of the target nucleic acid. In some embodiments, there are two base pair mismatches between the primer and the region of the target nucleic acid. In some embodiments, there are three base pair mismatches between the primer and the region of the target nucleic acid. In some embodiments, there are four base pair mismatches between the primer and the region of the target nucleic acid. In some embodiments, there are five base pair mismatches between the primer and the region of the target nucleic acid.

In some embodiments, the primer provided herein is labeled, e.g., for enrichment or detection of the amplified products. In some embodiments, the primer provided herein is labeled for detection by spectroscopic, photochemical, biochemical, immunochemical, or chemical means. In some embodiments, the primer is labeled with biotin, amine, radiolabels (e.g., 32P), fluorescent dyes, electron-dense reagents, enzymes (as commonly used in ELISAS), or biotin.

In some embodiments, the polymerase provided herein catalyzes incorporation of nucleotides to extend a 3' hydroxyl terminus of a primer molecule against a nucleic acid target sequence. In some embodiments, the reaction by the polymerase provided herein is performed in isothermal conditions. In some embodiments, the polymerase is a strand-displacing polymerase. Exemplary polymerases include but not limited to Bst DNA polymerase, 9° Nm DNA polymerase, Phi29 DNA polymerase, DNA polymerase I (*E. coli*), DNA polymerase I (Large)m, (Klenow) fragment, Klenow fragment (3'-5' exo-), T4 DNA polymerase, T7 DNA polymerase, Deep VentR™ (exo-) DNA polymerase, Deep VentR™ DNA polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo–) DNA Polymerase, RepliPHI™ Phi29 DNA Polymerase, rBst DNA Polymerase, rBst DNA Polymerase (Large), Fragment (IsoTherm™ DNA Polymerase), MasterAmp™ AmpliTherm™, DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, and ThermoPhi DNA polymerase. In some embodiments, the polymerase is selected from a group consisting of Bst, Bsu, and Phi29. As the polymerase extends the hybridized strand, it can be beneficial to include single-stranded binding protein (SSB). SSB may stabilize the displaced (non-template) strand. Thus, in some embodiments, the method provided herein can further include SSB protein.

As discussed, one advantage provided by the linear or exponential amplifications provided herein is that the amplifications can be performed under constant temperature or isothermal conditions. As used herein, the term "constant temperature," "isothermal conditions," or "isothermally" refers to a set of reaction conditions where the temperature of the reaction is kept essentially constant during the course of the amplification reaction. However, it is not necessary that the temperature be maintained at precisely one temperature. If the equipment used to maintain an elevated temperature allows the temperature of the reaction mixture to vary by a few degrees, this is not detrimental to the amplification reaction, and can still be considered to be an isothermal reaction. In some embodiments, the amplification reaction is run at a constant temperature between 20° ° C. to 70° C. In some embodiments, the amplification reaction is run at a constant temperature between 25° C. to 60° C. In some embodiments, the amplification reaction is run at a constant temperature between 40° ° C. to 55° C. In some embodiments, the amplification reaction is run at a constant temperature between 30° ° C. to 40° C. Exemplary amplification reaction temperatures include 30° C., 31° C., 32° C., 33° C., 34° C., 35° C., 36° C., 37° C., 38° C., 39° C., 40° C., 41° C., 42° C., 43° C., 44° C., 45° C., 46° ° C., 47° C., 48° C., 49° C., 50° C., 51° C., 52° C., 53° C., 54° C., 55° C., 56° C., 57° C., 58° C., 59° C., and 60° C. In one embodiment, the amplification reaction temperature is about 37° C.

In some embodiments, the time that the amplification reaction is run may vary from, for example, 1 minute to several hours until the desired amount of the amplification is achieved. In some embodiments, the time that the amplification reaction is 5 minutes to 1 hour. Exemplary times of the amplification reaction include 5 minutes, 10 minutes, 15 minutes, 20 minutes, 30 minutes, 40 minutes, 50 minutes, and 60 minutes.

In some embodiments, the present methods can be used in certain applications wherein detection and/or quantification of the amplified nucleic acid products are desired. The amplified target sequence can be detected by any method known to one of ordinary skill in the art.

In some embodiments, dyes that specifically stain double-stranded DNA can be used to detect or quantify the amplified products. In some embodiments, intercalating dyes exhibit enhanced fluorescence upon binding to DNA or RNA. In some embodiments, dyes can be, for example, DNA or RNA intercalating fluorophores. Exemplary DNA or RNA intercalating fluorophores include but are not limited to Acridine orange, ethidium bromide, Hoechst dyes, PicoGreen, propidium iodide, SYBR I (an asymmetrical cyanine dye), SYBR II, TOTO (a thiaxole orange dimer) and YOYO (an oxazole yellow dimer).

In some embodiments, amplified products with specific sizes can be detected by gel electrophoresis. In some embodiments, the nucleotides used in the amplification reaction, can be labeled, e.g., with biotin. Biotin-labeled amplified sequences can be captured using avidin bound to a signal generating enzyme, for example, peroxidase.

In some embodiments, labeled nucleotides can be incorporated directly into the target sequence or into primers containing complementary sequences to the target of interested. Such labels can be radioactive and/or fluorescent in nature and can be resolved in any of the manners discussed herein.

Methods of detecting and/or continuously monitoring the amplification of nucleic acid products are also well known to those skilled in the art. For example, in some embodiments, the production or presence of target nucleic acids and nucleic acid sequences may be detected and monitored by Molecular Beacons. Molecular Beacons are hairpin shaped oligonucleotides containing a fluorophore on one end and a quenching dye on the opposite end. The loop of the hair-pin contains a probe sequence that is complementary to a target sequence and the stem is formed by annealing of complementary arm sequences located on either side of the probe sequence. When the molecular beacon encounters a target molecule, hybridization occurs; the loop structure is converted to a stable more rigid conformation causing separation of the fluorophore and quencher molecules leading to fluorescence. Tyagi et al., Nature Biotechnology, 1996, 303-308. Thus, the generation of fluorescence indicates the synthesis of the intended amplified product. For another example, in some embodiments, the production or presence of target nucleic acids and nucleic acid sequences can be detected and monitored by Fluorescence resonance energy transfer (FRET). FRET is a useful tool to quantify molecular dynamics, for example, in DNA-DNA interactions. For monitoring the production of a specific product a probe can be labeled with a donor molecule on one end and an acceptor molecule on the other. Probe-target hybridization brings a change in the distance or orientation of the donor and acceptor and FRET change is observed. Lakowicz, "Principles of Fluorescence Spectroscopy," Plenum Publishing Corporation, 2nd edition (Jul. 1, 1999). Other exemplary methods for detecting and/or continuously monitoring the amplification of nucleic acid products include but not limited to Mass Spectrometry, capillary gel electrophoresis, sequencing, and various surface capture methods as known to those skilled in the art. In some embodiments, running the amplification reaction with asymmetric amounts of primers, i.e., with one primer present in higher concentration than the other, would permit amplification with a bias towards one strand. An excess of a single strand may facilitate detection by such modalities as Molecular Beacons, which detect ssDNA.

The amplification methods provided herein can be used in various applications. For example, in some embodiments, the method provided herein can be used to isolate DNA fragments from genomic DNA by selective amplification of a specific region of DNA.

For another example, in some embodiments, the amplification methods provided herein can be used for diagnosing various diseases based on the production or presence of a target nucleic acid linked to a specific disease. In some embodiments, the methods provided herein can be used for early diagnosis of malignant diseases, e.g., leukemia and lymphomas. In other embodiments, methods provided herein can be used directly on genomic DNA samples to amplify and detect translocation-specific malignant cells.

In other embodiments, the methods provided herein can be used for diagnosis of infectious diseases, including those caused by bacteria or viruses. For example, the present methods can be used to detect infectious agents and distinguish non-pathogenic from pathogenic strains by virtue of specific nucleic acid sequence. In some embodiments, the amplification methods provided herein can amplify and identify non-cultivatable or slow-growing microorganisms, e.g., mycobacteria, anaerobic bacteria, or viruses from tissue culture assays and animal models. In other embodiments, the amplification methods provided herein can amplify and identify viral DNA in a sample from an individual.

In yet other embodiments, the present amplification methods can be used to generate nucleic acid materials to augment other procedures. For example, in some embodiments, the present amplification methods can be used for generating hybridization probes for Southern or northern hybridization and DNA cloning, which require relatively larger amounts of DNA, representing a specific DNA region. For another example, the methods provided herein can be used for nucleic acid sequencing.

In a specific embodiment, the CRISPR-Cas mediated nucleic acid amplification methods provided herein can be used for amplifying a library of nucleic acid fragments, e.g., generated using library preparation methods and/or kits available from Illumina, Inc. (San Diego, CA).

In some embodiments, the methods provided herein can be used to amplify a library of nucleic acid fragments generated from genomic DNA. In a specific embodiment, the library of nucleic acid fragments is generated using tagmentation. In a specific embodiment, the library of nucleic acid fragments is generated from genomic DNA using Illumina's Nextera library preparation methods and kits (available from Illumina, Inc, San Diego, CA).

Thus, in some embodiments, the method provided herein further includes applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments, and thus incorporates a universal primer sequence into each of the plurality of target nucleic acid fragments, wherein the crRNA or the derivative thereof contains a target-specific nucleotide region complementary to a region of the universal primer.

In some embodiments, the target nucleic acid is subjected to a transposase mediated tagmentation that results in fragmentation of the target nucleic acid and ligation of adaptors to the 5' end of both strands of double-stranded DNA fragments. Optionally, the target nucleic acid can be fragmented and adaptors can be added to the 5' and 3' ends using tagmentation or transposition as described in U.S. Publication No. 2010/0120098, which is incorporated by reference herein in its entirety. Briefly, a transposition reaction is a reaction wherein one or more transposons are inserted into target nucleic acids at random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. Exemplary transposition complexes, suitable for use in the methods provided herein, include, but are not limited to, those formed by a hyperactive Tn5 transposase and a Tn5-type transposon end or by a MuA transposase and a Mu transposon end comprising R1 and R2 end sequences (see, e.g., Goryshin and Reznikoff, *J. Biol. Chem.* 273: 7367, 1998; and Mizuuchi, *Cell* 35: 785, 1983; Savilahti et al., *EMBO J.* 14: 4893, 1995; which are incorporated by reference herein in their entireties). However, any transposition system that is capable of inserting a transposon end with sufficient efficiency to tag target nucleic acids for its intended purpose can be used in the provided methods. Other examples of known transposition systems that could be used in the provided methods include, but are not limited to, *Staphylococcus aureus* Tn552, Ty1, Transposon Tn7, Tn/O and IS10, Mariner transposase, Tel, P Element, Tn3, bacterial insertion sequences, retroviruses, and retrotransposon of yeast (see, e.g., Colegio et al., 2001, *J. Bacteriol.* 183: 2384-8; kirby et al., 2002, *Mol. Microbiol.* 43: 173-86; Devine and Boeke, 1994, *Nucleic Acids Res.*, 22: 3765-72; International Patent Application No. WO 95/23875; Craig, 1996, *Science* 271: 1512; Craig, 1996, Review in: *Curr Top Microbiol Immunol.* 204: 27-48; Kleckner et al., 1996, *Curr Top Microbiol Immunol.* 204: 49-82; Lampe et al., 1996, *EMBO J.* 15: 5470-9; Plasterk, 1996, *Curr Top Microbiol Immunol* 204: 125-43; Gloor, 2004, *Methods Mol. Biol.* 260: 97-114; Ichikawa and Ohtsubo, 1990, *J Biol. Chem.* 265: 18829-32; Ohtsubo and Sekine, 1996, *Curr. Top. Microbiol. Immunol.* 204: 1-26; Brown et al., 1989, *Proc Natl Acad Sci USA* 86: 2525-9; Boeke and Corces, 1989, *Annu Rev Microbiol.* 43: 403-34; which are incorporated herein by reference in their entireties). In some embodiments, the method of the present disclosure further comprises removing the transposase enzyme and adding to the ends of the adapted DNA fragments by PCR.

The term "tagmentation," "tagment," or "tagmenting," as used herein, refers to transforming a nucleic acid, e.g., a DNA, into adaptor-modified templates in solution ready for cluster formation and sequencing by the use of transposase mediated fragmentation and tagging. This process often involves the modification of the nucleic acid by a transposome complex comprising transposase enzyme complexed with adaptors comprising transposon end sequence. Tagmentation results in the simultaneous fragmentation of the nucleic acid and ligation of the adaptors to the 5' ends of both strands of duplex fragments. Following a purification step to remove the transposase enzyme, additional sequences are added to the ends of the adapted fragments by PCR.

The term "transposome complex," as used herein, refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in the present invention. In particular embodiments, a preferred transposition system is capable of inserting the transposon end in a random or in an almost random manner to 5'-tag and fragment the target nucleic acid.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further comprise additional sequences (e.g., adaptor or primer sequences) as needed or desired. In some embodiments, the method provided herein is exemplified by employing a transposition complex formed by a hyperactive Tn5 transposase and a Tn5-type transposon end (Goryshin and Reznikoff, 1998, *J. Biol. Chem.*, 273: 7367) or by a MuA transposase and a Mu transposon end comprising R1 and R2 end sequences (Mizuuchi, 1983, *Cell*, 35: 785; Savilahti et al., 1995, *EMBO J.*, 14: 4893). However, any transposition system that is capable of inserting a transposon end in a random or in an almost random manner with sufficient efficiency to 5'-tag and fragment a target DNA for its intended purpose can be used in the present invention. Examples of transposition systems known in the art which can be used for the present methods include but are not limited to *Staphylococcus aureus* Tn552 (Colegio et al., 2001, *J Bacteriol.*, 183: 2384-8; Kirby et al., 2002, *Mol Microbiol*, 43: 173-86), TyI (Devine and Boeke, 1994, *Nucleic Acids Res.*, 22: 3765-72 and International Patent Application No. WO 95/23875), Transposon Tn7 (Craig, 1996, *Science.* 271: 1512; Craig, 1996, Review in: *Curr Top Microbiol Immunol*, 204: 27-48), TnlO and ISIO (Kleckner et al., 1996, *Curr Top Microbiol Immunol*, 204: 49-82), Mariner transposase (Lampe et al., 1996, *EMBO J.*, 15: 5470-9), Tci (Plasterk, 1996, *Curr Top Microbiol Immunol*, 204: 125-43), P Element (Gloor, 2004, *Methods Mol Biol*, 260: 97-114), TnJ (Ichikawa and Ohtsubo, 1990, *J Biol Chem.* 265: 18829-32), bacterial insertion sequences (Ohtsubo and Sekine, 1996, *Curr. Top. Microbiol. Immunol.* 204:1-26), retroviruses (Brown et al., 1989, *Proc Natl Acad Sci USA*, 86: 2525-9), and retrotransposon of yeast (Boeke and Corces, 1989, *Annu Rev Microbiol.* 43: 403-34). The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase.

The term "transposon end" (TE) refers to a double-stranded nucleic acid, e.g., a double-stranded DNA, that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is sometimes used in the present disclosure in connection with the composition of transposon ends, it should be understood that any suitable nucleic acid or nucleic acid analogue can be utilized in a transposon end.

Through an in vitro transposition reaction, target nucleic acid fragments are tagged at the 5' end. In some embodiments, the method provided herein further includes steps to incorporate a 3' end tag to the 5' tagged nucleic acid fragments to make a library of di-tagged nucleic acid fragments. Adding 3' end tag can be performed through various methods, e.g., by using DNA polymerase, terminal transferase, and/or ligase as described in WO 2010/048605 the content of which is incorporated by its entirety.

In some embodiments, di-tagged nucleic acid fragments are generated by using a polymerase, e.g., a DNA polymerase, with strand-displacement or 5' nuclease activity. In some embodiments, the method provided herein includes incubating the population of annealed 5'-tagged nucleic acid fragments with a DNA polymerase that has strand-displacement or 5' nuclease activity under conditions without thermocycling and wherein the annealed 5'-tagged nucleic acid fragments are not denatured, wherein the DNA polymerase extends the 3'-end of each strand of the annealed 5'-tagged nucleic acid fragments using the complementary strand as a template and displaces or digests the non-transferred strand, thereby generating the library of di-tagged double-stranded DNA fragments.

In other embodiments, the 5'-tagged nucleic acid fragments are incubated with a DNA polymerase consisting of a terminal transferase and at least one substrate for the terminal transferase under conditions and for sufficient time wherein the terminal transferase joins the second tag to the 3' end of the 5'-tagged nucleic acid fragments, thereby generating a library of di-tagged nucleic acid fragments. In some embodiments, the 3'-end of the non-transferred transposon end that composes the transposon end composition is blocked (e.g., by using a non-transferred transposon end that has a dideoxy nucleotide or a 3'-O-methyl-nucleotide as the 3'-terminal nucleotide).

In yet other embodiments, di-tagged nucleic acid fragments are generated by using a template-dependent ligase and a ligation tagging oligonucleotide. In some embodiments, the 5'-tagged nucleic acid fragments are incubated with a template-dependent DNA ligase and a ligation tagging oligodeoxynucleotide having a 3'-portion and a 5'-portion, wherein the 3'-portion exhibits a second tag that exhibits any sequence that is desired to be joined to the 3'-end of the 5'-tagged DNA fragments and the 5'-portion has a 5'-monophosphate group and exhibits a random sequence, under conditions and for sufficient time wherein the second tag is joined to the annealed 5'-tagged DNA fragments, thereby generating a library of DNA fragments comprising annealed di-tagged DNA fragments.

In some embodiments, the nucleic acid fragments generated contain universal sequences at the two ends of the nucleic acid fragments. The universal sequences at the two ends of the nucleic acid fragments, e.g., in a library, can be targeted to by the CRISPR-Cas system according the methods provided herein, and as such the fragments can be amplified, e.g., in a cluster formation reaction.

Such universal sequences can be introduced into the two ends of the nucleic acid fragments in a library by a PCR or Nextera transposon reaction. In some embodiments, after a library of tagged nucleic acid fragments is generated, the tagged nucleic acid fragments can be amplified, e.g., using limited-cycle polymerase chain reaction (PCR), to introduce other end sequences or adaptors, e.g., index, universal primers and other sequences required for cluster formation and sequencing. In a specific embodiment, a limited-cycle PCR amplification is performed to add index 1 (P7) and index 2 (P5) (available from Illumina, Inc, San Diego, CA) to the two ends of the nucleic acid fragments.

In some embodiments, such amplification is performed to a library of 5' tagged nucleic acid fragments. In some embodiments, such amplification is performed to a library of di-tagged nucleic acid fragments. Exemplary amplification methods include polymerase chain reaction (PCR), strand-displacement amplification reaction, rolling circle amplification reaction, ligase chain reaction, transcription-mediated amplification reaction, and loop-mediated amplification reaction.

In some embodiments, the method provided herein includes amplifying the library of di-tagged nucleic acid fragments using a PCR. In some embodiments, provided herein includes amplifying the library of di-tagged nucleic acid fragments using the Cas9 mediated amplification method provided herein. In some embodiments, the method provided herein uses single-primer PCR amplification of a library of di-tagged DNA fragments. In some embodiments, the step of amplifying di-tagged DNA fragments includes using a DNA polymerase and at least one primer that is complementary to the second tag. In some embodiments, the step of amplifying the library of di-tagged DNA fragments includes amplifying the library of tagged DNA fragments by PCR using only one oligodeoxyribonucleotide that exhibits the sequence of at least a portion of the transferred strand as a PCR primer and the di-tagged DNA fragments as templates. In some embodiments, the primer contains a 5' portion that contains additional sequence, e.g., an adaptor sequence.

In some embodiments, two different PCR primers are used, each of which PCR primers exhibits the sequence of at least a portion of the transferred transposon end that composes the transposon end composition. In some embodiments, each PCR primer includes a 3'-portion and a 5'-portion, wherein the 3'-portion exhibits the respective transferred transposon end sequence and the 5'-portion exhibits the sequence of a respective tag domain or an adaptor for a particular purpose (e.g., a sequencing tag domain/adaptor or an amplification tag domain/adaptor, and optionally an address tag domain/adaptor for next-generation sequencing or amplification). For example, when a single transposon end composition is used in the in vitro transposition reaction to generate the library of di-tagged DNA fragments using a DNA polymerase that has strand-displacement or 5' nuclease activity, the di-tagged DNA fragments can be amplified by PCR using two different PCR primers. Each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain/adaptor or an amplification tag domain/adaptor, and optionally an address tag domain/adaptor for next-generation sequencing or amplification). In some embodiments, the 5' portion of each PCR primer is different from that of the other primer, and as such the sequences of the two ends of the PCR product are different. For example, one end contains one index and/or universal primer sequence, and the other end contains a different index and/or universal primer sequence.

In some embodiments, the two ends of di-tagged nucleic acid fragments originate from two different transferred strand sequences. For example, in some embodiments, two different transposomes can be used in the in vitro transposition reaction, and each of the two transposomes contains the same transposase but a different transposon end composition. In some embodiments, two different transposomes are used, and the two different transposomes each contains the same transposase and the transposon end compositions contain different transferred strands. In some embodiments, two different transposomes are used, and each of the two transposomes includes different transposase enzymes and different transposon end compositions, each of which forms a functional complex with the respective transposase. In some embodiments, wherein two different transposon end compositions are used in the in vitro transposition reaction, and the library of di-tagged single stranded nucleic acid fragments is generated using a DNA polymerase that has strand-displacement or 5' nuclease activity, the first tag exhibits the sequence of the transferred strand of one transposon end composition and the second tag exhibits the sequence of the non-transferred strand of the other transposon end composition.

In the above mentioned embodiments and other embodiments wherein two different transferred strands are linked to the 5' end of each opposite strands of the double stranded nucleic acid, the method provided herein can further include the step of amplifying the di-tagged nucleic acid fragments by PCR using two different PCR primers. One of the PCR primers exhibits the sequence of at least a portion of one transferred strand that compose one transposon end composition, and the other of PCR primers exhibits the sequence of at least a portion of the other transferred strand that composes the other transposon end composition.

In some embodiments wherein two primers are used, each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain or an amplification tag domain, and optionally an address tag domain for next-generation sequencing or amplification). In some embodiments, the 5' portion of each PCR primer is different from that of the other primer, and as such to introduce different sequences to the two ends of the PCR product. In some embodiments, the 5' portion of the first PCR primer or the 5' portion of the second PCR primer, or the 5' portions of both the first and the second PCR primers contain first or second sequencing tags/adaptors, respectively, for generation of templates for next-generation sequencing for a particular sequencing platform (e.g., sequencing tags for an Illumina Nextera sequencing platform). In some embodiments, the 5' portion of the first PCR primer or the 5' portion of the second PCR primer additionally contains an address tag domain/adaptor or another tag domain/adaptor for a particular purpose.

A wide variety of enzymes and kits are available for performing the amplification reaction by PCR as known by those skilled in the art. For example, in some embodiments, the PCR amplification is performed using either the FAIL-SAFE™ PCR System or the MASTERAMP™ Extra-Long PCR System from EPICENTRE Biotechnologies, Madison, WI, as described by the manufacturer. However, the present disclosure is not limited to the use of those products or conditions for the amplification reaction and any suitable thermostable DNA polymerase and reaction mixture that permits amplification of the sequence between the primer that anneals to the target sequence and the primer that anneals to the transposon can be used.

The method provide herein is not limited to the use of PCR to amplify the library of tagged nucleic acid fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present invention. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523, 204; 5,536,649; 5,624,825; 5,631, 147; 5,648,211; 5,733, 752; 5,744,311; 5,756, 702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214, 587 of Gen-Probe, Inc.; U.S. Pat. No. 6,063,604 of Wick et al; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi. In some embodiments, Cas mediated amplification provided herein is used to amplify the library of the target nucleic acid fragments.

In some embodiments, when the target nucleic acid has a universal primer sequence, e.g., as generated using the methods provided above, a guide RNA, e.g., a crRNA, can target to the universal primer sequence of the nucleic acid fragments in the library so that to amplify the library of nucleic acid fragments isothermally.

FIG. 1 illustrates a method to amplify nucleic acid fragments generated by Nextera library preparation (available from Illumina, Inc., San Diego, CA) according to the present disclosure. In some embodiments, the Cas proteins provided herein require a PAM sequence in order to recognize a target. For example, Cas9 protein requires a sequence of the motif NGG residing adjacent to the target sequence. A sequence complementary to the PAM sequence can be incorporated into the flowcell primers (e.g., P5 and P7) that are added to library inserts to result in PAM modified P5 and P7 primers capable of targeting PAM-containing sequences. The sequences of standard universal primers P5 and P7 are shown in FIG. 1A (SEQ ID No.1 and SEQ ID No. 2). The sequences of PAM-modified primers P5 and P7 are also shown in FIG. 1A (SEQ ID No.3 and SEQ ID No. 4). Thus, in some embodiments, PAM-modified primers P5 and P7 are added to nucleic acid fragments in the library. In a specific embodiment, PAM-modified primers P5 and P7 are added to nucleic acid fragments using a limited-cycle PCR.

Figure 1C:
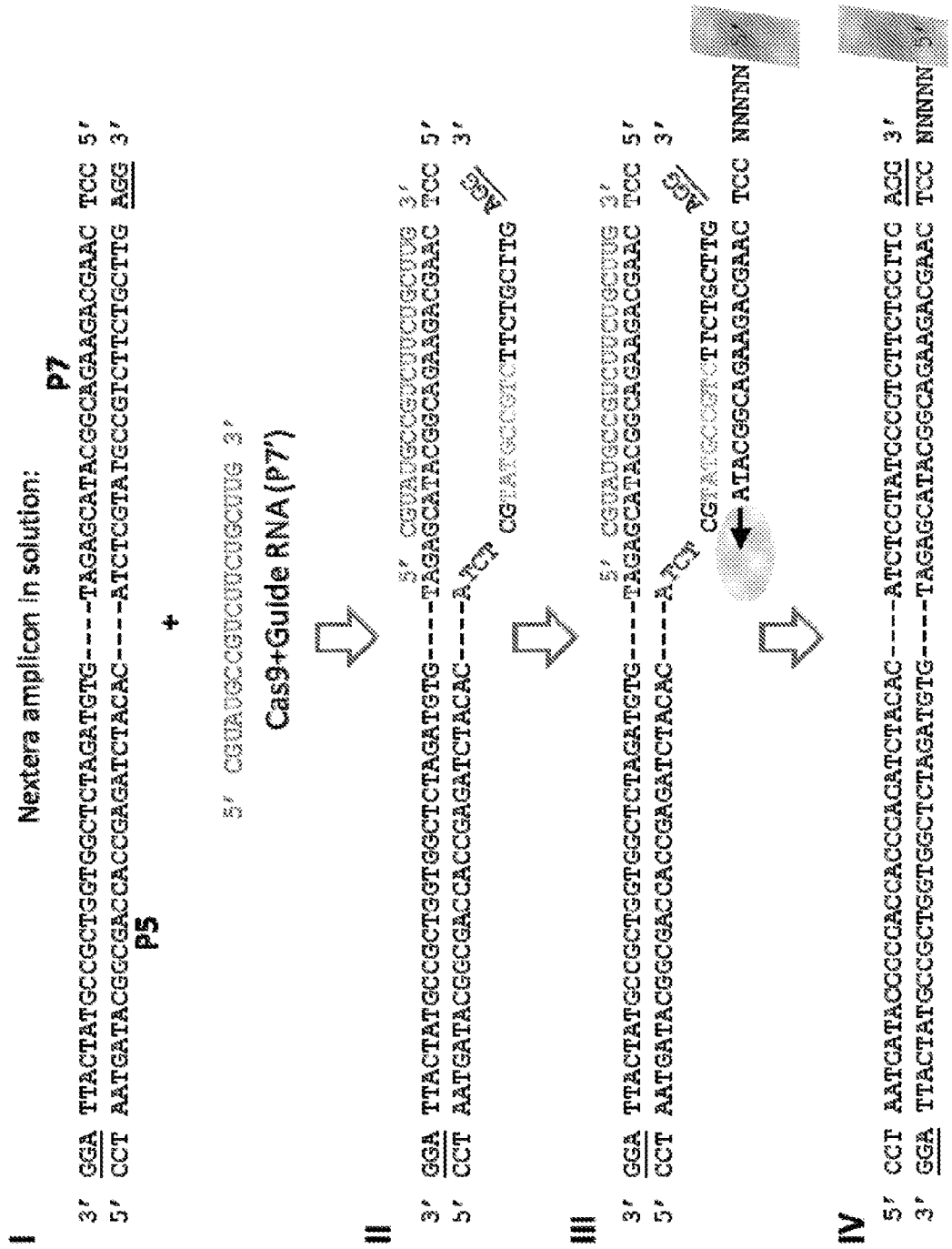
FIG. 1C illustrates one round of Cas9-mediated linear amplification using a crRNA targeting a modified P7 primer. Panel (I) depicts the DNA to be amplified which possesses appropriate primer sequences P5 (SEQ ID NO:09) and P7 (SEQ ID NO:10). The guide RNA targeting P7, bound to Cas9, is also shown as P7' (SEQ ID NO:08). Panel (II) shows the R loop created by Cas9 after the guide RNA has hybridized to the first strand. Panel (III) illustrates the immobilized P7 primer (SEQ ID NO: 14) hybridizing to the displaced second strand, followed by polymerase extension. Panel (IV) shows the resulting extended primer P7 (SEQ ID NO: 15) at 5' end of the amplicon and a P5 sequence (SEQ ID NO:03) at 3' end of the amplicon. The resulting amplicon can be re-targeted by Cas9+crRNA as shown in the step depicted in panel (II). With both sides of the amplicon undergoing amplification (FIGS. 1B and 1C), exponential amplification can be achieved.

As shown in FIG. 1B-C, DNA fragments (e.g., Nextera amplicons in solution) contain P5 and P7 primer sequences (SEQ ID No. 1 and SEQ ID No.2) at the ends of the amplicon. A CRISPR-Cas9 system containing a guide RNA of SEQ ID No. 7 targeting a region of P5 primer sequence (see FIG. 1B), and a CRISPR-Cas9 system containing a guide RNA of SEQ ID No. 8 targeting a region of P7 primer sequence (see FIG. 1C) are added. The CRISPR-Cas9 systems open some regions of double-stranded DNA to create R-loop structures near the two ends of the DNA fragment by binding crRNA to the primer sequences. Then truncated PAM-modified P5 and P7 primers (SEQ ID No. 5 and SEQ ID No.6) can be used to amplify the DNA fragment.

Thus, in some embodiments, the first strand of the target double-stranded nucleic acid contains a universal sequence, and wherein the crRNA or the derivative thereof contains a sequence complementary to a region of the universal sequence. In some embodiments, the primer contains a sequence of a region of the universal sequence.

In some embodiments, the universal primer has a sequence of SEQ ID No. 3. In some embodiments, the crRNA contains a sequence of SEQ ID No.7. In some embodiments, the primer contains a sequence of SEQ ID No. 5.

In some embodiments, the universal primer sequence has a sequence of SEQ ID No. 4. In some embodiments, the crRNA contains a sequence of SEQ ID No.8. In some embodiments, the primer contains a sequence of SEQ ID No. 6.

In some embodiments, the first strand of the target double-stranded nucleic acid contains a first universal sequence, and wherein the crRNA or the derivative thereof of the first system contains a sequence complementary to a region of the first universal sequence, and the second strand of the target double-stranded nucleic acid contains a second universal sequence, and wherein the crRNA or the derivative thereof of the second system contains a sequence complementary to a region of the second universal sequence. In some embodiments, the first primer contains a sequence of a region of the first universal sequence, and the second primer contains a sequence of a region of the second universal sequence. In a specific embodiment, the first universal sequence has a sequence of SEQ ID No. 3, the crRNA or the derivative thereof of the first system contains a sequence of SEQ ID No.7, and the first primer contains a sequence of SEQ ID NO.5, and the second universal sequence has a sequence of SEQ ID No. 4, the crRNA or derivative thereof of the second system contains a sequence of SEQ ID No.8, and the second primer contains a sequence of SEQ ID NO.6.

The methods provided herein can be used in isothermal amplification for sequencing, e.g., in a cluster amplification developed by Illumina, Inc. (San Diego, CA). In some embodiments, the target nucleic acid of the present methods can be immobilized on a surface for amplification. For example, in some embodiments, immobilized nucleic acid fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR whether one or both primers of each pair of amplification primers are immobilized.

As used herein, the terms "solid surface," "solid support" and other grammatical equivalents herein refer to any material that is appropriate for or can be modified to be appropriate for the attachment of a polynucleotide. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, solid supports and solid surfaces are located within a flow cell apparatus. In some embodiments, the solid support comprises a patterned surface suitable for immobilization of molecules in an ordered pattern. A "patterned surface" refers to an arrangement of different regions in or on an exposed layer of a solid support. In some embodiments, the solid support comprises an array of wells or depressions in a surface. The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/ 0108082, each of which is incorporated herein by reference. In some embodiments, the solid support or its surface is non-planar, such as the inner or outer surface of a tube or vessel. In some embodiments, the solid support comprises microspheres or beads. "Microspheres," "beads," "particles," or grammatical equivalents herein are intended to mean small discrete particles made of various material including, but are not limited to, plastics, ceramics, glass, and polystyrene. In certain embodiments, the microspheres are magnetic microspheres or beads. Alternatively or additionally, the beads may be porous. The bead sizes range from nanometers, e.g. 100 nm, to millimeters, e.g. 1 mm.

In other embodiments, the immobilized nucleic acid fragments are amplified in solution. For example, in some embodiments, the immobilized nucleic acid fragments are cleaved or otherwise liberated from the solid support and amplification primers are then hybridized in solution to the liberated molecules. In other embodiments, amplification primers are hybridized to the immobilized nucleic acid fragments for one or more initial amplification steps, followed by subsequent amplification steps in solution. Thus, in some embodiments an immobilized nucleic acid template can be used to produce solution-phase amplicons. It will be appreciated that any of the amplification methodologies described herein can be utilized with universal or target-specific primers to amplify immobilized nucleic acid fragments.

The nucleic acid amplified according to the method provided herein can be sequenced according to any suitable sequencing methodology, such as direct sequencing, including sequencing by synthesis, sequencing by ligation, sequencing by hybridization, nanopore sequencing and the like. In some embodiments, the immobilized DNA fragments are sequenced on a solid support. In some embodiments, the solid support for sequencing is the same solid support upon which the amplification occurs.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., 1996, Analytical Biochemistry 242 (1), 84-9; Ronaghi, 2001, Genome Res. 11(1), 3-11; Ronaghi et al., 1998, Science 281(5375), 363; U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al., 2003, *Science* 299, 682-686; Lundquist et al., 2008, *Opt. Lett.* 33, 1026-1028; Korlach et al., 2008, *Proc. Natl. Acad. Sci. USA* 105, 1176-1181, the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al., 2000, *Trends Biotechnol.*, 18, 147-151; Deamer et al., 2002, *Acc. Chem. Res.* 35:817-825; Li et al., 2003, Nat. Mater. 2:611-615), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al., 2007, *Clin. Chem.*, 53, 1996-200; Healy, 2007, Nanomed. 2, 459-481; Cockroft et al., 2008, *J. Am. Chem. Soc.*, 130, 818-820, the disclosures of which are incorporated herein by reference). In other nanopore sequencing embodiments, the DNA fragment to be sequenced creates a unique nanopore current signature using gamma phosphate modified nucleotides.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for amplifying a target double-stranded nucleic acid comprising a first strand and a second strand, comprising:
    (a) providing a system comprising: a clustered regularly interspaced short palindromic repeats (CRISPR) RNA (crRNA) and a CRISPR-associated (Cas) protein, wherein the crRNA contains a target-specific nucleotide region complementary to a region of the first strand;
    (b) contacting the target double-stranded nucleic acid with the system to form a complex comprising a displaced region of the second strand;
    (c) hybridizing a primer to the displaced region, wherein the primer is immobilized on a substrate, and wherein the primer comprises a sequence complementary to the displaced region, and
    (d) extending a nucleic acid complementary to the second strand from the primer using a polymerase.

2. The method of claim 1, wherein the substrate comprises a flow cell.

3. The method of claim 1, wherein the substrate comprises a bead.

4. The method of claim 1, further comprising repeating step (a) to step (d).

5. The method of claim 4, wherein the target double-stranded nucleic acid is exponentially amplified.

6. The method of claim 1, wherein the system is selected from the group consisting of a Type I CRISPR-Cas system, a Type II CRISPR-Cas system, and a Type III CRISPR-Cas system.

7. The method of claim 1, wherein the first strand of the target double-stranded nucleic acid comprises a sequence complementary to a 5'-NGG protospacer-adjacent motif (PAM).

8. The method of claim 1, wherein the first strand of the target double-stranded nucleic acid comprises a universal sequence, and the primer comprises a sequence of a region of the universal sequence.

9. The method of claim 8, wherein the universal sequence comprises the sequence of SEQ ID NO:03 or SEQ ID NO:04.

10. The method of claim 1, wherein the primer comprises the sequence of SEQ ID NO:05 or SEQ ID NO:06.

11. The method of claim 1, wherein the polymerase is a strand-displacing polymerase selected from the group consisting of Bst, Bsu, and Phi29.

12. The method of claim 1, further comprising:
    providing a second system comprising: a second crRNA and a second Cas protein, wherein the second crRNA comprises a target-specific nucleotide region complementary to a region of the second strand;
    contacting the target double-stranded nucleic acid with the second system;
    hybridizing a second primer to the first strand contacted with the second system, and
    extending the hybridized second primer.

13. The method of claim 1, wherein the system further comprises a trans-activating crRNA (tracrRNA).

14. The method of claim 13, wherein the crRNA is fused to the tracrRNA.

15. The method of claim 1, wherein the crRNA comprises the sequence of SEQ ID NO: 07 or 08.

16. The method of claim 1, wherein the target double-stranded nucleic acid comprises the sequence of SEQ ID NO:09 or 10.

17. The method of claim 1, wherein the primer comprises the sequence of SEQ ID NO:12 or 14.

* * * * *

SEQUENCE LISTING

```
<160> NUMBER OF SEQ ID NOS: 15

<210> SEQ ID NO 1
<211> LENGTH: 29
<212> TYPE: DNA
<213> ORGANISM: Artificial Sequence
<220> FEATURE:
<223> OTHER INFORMATION: Standard P5 sequence

<400> SEQUENCE: 1
aatgatacgg cgaccaccga gatctacac                                          29

<210> SEQ ID NO 2
<211> LENGTH: 24
<212> TYPE: DNA
<213> ORGANISM: Artificial Sequence
<220> FEATURE:
<223> OTHER INFORMATION: Standard P7 sequence

<400> SEQUENCE: 2
caagcagaag acggcatacg agat                                               24

<210> SEQ ID NO 3
<211> LENGTH: 32
<212> TYPE: DNA
<213> ORGANISM: Artificial Sequence
<220> FEATURE:
<223> OTHER INFORMATION: PAM-Modified P5 sequence
<220> FEATURE:
<221> NAME/KEY: misc_feature
<222> LOCATION: 3
<223> OTHER INFORMATION: n = A,T,C or G
```

```
<400> SEQUENCE: 3
ccnaatgata cggcgaccac cgagatctac ac                                32

<210> SEQ ID NO 4
<211> LENGTH: 27
<212> TYPE: DNA
<213> ORGANISM: Artificial Sequence
<220> FEATURE:
<223> OTHER INFORMATION: PAM-Modified P7 sequence
<220> FEATURE:
<221> NAME/KEY: misc_feature
<222> LOCATION: 3
<223> OTHER INFORMATION: n = A,T,C or G

<400> SEQUENCE: 4
ccncaagcag aagacggcat acgagat                                      27

<210> SEQ ID NO 5
<211> LENGTH: 21
<212> TYPE: DNA
<213> ORGANISM: Artificial Sequence
<220> FEATURE:
<223> OTHER INFORMATION: Truncated PAM-Modified P5 sequence
<220> FEATURE:
<221> NAME/KEY: misc_feature
<222> LOCATION: 3
<223> OTHER INFORMATION: n = A,T,C or G

<400> SEQUENCE: 5
ccnaatgata cggcgaccac c                                            21

<210> SEQ ID NO 6
<211> LENGTH: 21
<212> TYPE: DNA
<213> ORGANISM: Artificial Sequence
<220> FEATURE:
<223> OTHER INFORMATION: Truncated PAM-Modified P7 sequence
<220> FEATURE:
<221> NAME/KEY: misc_feature
<222> LOCATION: 3
<223> OTHER INFORMATION: n = A,T,C or G

<400> SEQUENCE: 6
ccncaagcag aagacggcat a                                            21

<210> SEQ ID NO 7
<211> LENGTH: 20
<212> TYPE: RNA
<213> ORGANISM: Artificial Sequence
<220> FEATURE:
<223> OTHER INFORMATION: Guide RNA P5 targeting

<400> SEQUENCE: 7 ucggggucg ccguaucauu                                               20

<210> SEQ ID NO 8
<211> LENGTH: 20
<212> TYPE: RNA
<213> ORGANISM: Artificial Sequence
<220> FEATURE:
<223> OTHER INFORMATION: Guide RNA P7 targeting

<400> SEQUENCE: 8
cguaugccgu cuucugcuug                                              20

<210> SEQ ID NO 9
<211> LENGTH: 32
```

```
<212> TYPE: DNA
<213> ORGANISM: Artificial Sequence
<220> FEATURE:
<223> OTHER INFORMATION: DNA to be amplified which possesses primer
      sequence P5

<400> SEQUENCE: 9
cctaatgata cggcgaccac cgagatctac ac                              32

<210> SEQ ID NO 10
<211> LENGTH: 27
<212> TYPE: DNA
<213> ORGANISM: Artificial Sequence
<220> FEATURE:
<223> OTHER INFORMATION: DNA to be amplified which possesses primer
      sequence P7

<400> SEQUENCE: 10
atctcgtatg ccgtcttctg cttgagg                                    27

<210> SEQ ID NO 11
<211> LENGTH: 19
<212> TYPE: RNA
<213> ORGANISM: Artificial Sequence
<220> FEATURE:
<223> OTHER INFORMATION: guide RNA targeting P5

<400> SEQUENCE: 11
uuacuaugcc gugguggcu                                             19

<210> SEQ ID NO 12
<211> LENGTH: 26
<212> TYPE: DNA
<213> ORGANISM: Artificial Sequence
<220> FEATURE:
<223> OTHER INFORMATION: includes immobilized P5 primer
<220> FEATURE:
<221> NAME/KEY: misc_feature
<222> LOCATION: 1, 2, 3, 4, 5
<223> OTHER INFORMATION: n = A,T,C or G

<400> SEQUENCE: 12
nnnnncctaa tgatacggcg accacc                                     26

<210> SEQ ID NO 13
<211> LENGTH: 37
<212> TYPE: DNA
<213> ORGANISM: Artificial Sequence
<220> FEATURE:
<223> OTHER INFORMATION: extended primer P5
<220> FEATURE:
<221> NAME/KEY: misc_feature
<222> LOCATION: 1, 2, 3, 4, 5
<223> OTHER INFORMATION: n = A,T,C or G

<400> SEQUENCE: 13
nnnnncctaa tgatacggcg accaccgaga tctacac                         37

<210> SEQ ID NO 14
<211> LENGTH: 26
<212> TYPE: DNA
<213> ORGANISM: Artificial Sequence
<220> FEATURE:
<223> OTHER INFORMATION: includes immobilized P7 primer
<220> FEATURE:
<221> NAME/KEY: misc_feature
<222> LOCATION: 1, 2, 3, 4, 5
<223> OTHER INFORMATION: n = A,T,C or G
```

```
<400> SEQUENCE: 14
nnnnntccca agcagaagac ggcata                                              26

<210> SEQ ID NO 15
<211> LENGTH: 32
<212> TYPE: DNA
<213> ORGANISM: Artificial Sequence
<220> FEATURE:
<223> OTHER INFORMATION: Includes extended primer P7
<220> FEATURE:
<221> NAME/KEY: misc_feature
<222> LOCATION: 1, 2, 3, 4, 5
<223> OTHER INFORMATION: n = A,T,C or G

<400> SEQUENCE: 15
nnnnntccca agcagaagac ggcatacgag at                                       32
```